and(12) United States Patent
Kharbanda et al.

(10) Patent No.: US 8,129,506 B2
(45) Date of Patent: Mar. 6, 2012

(54) MODULATION OF THE INTERACTION OF MUC1 WITH MUC1 LIGANDS

(75) Inventors: Surender Kharbanda, Natick, MA (US); Donald W. Kufe, Wellesley, MA (US)

(73) Assignees: Genzyme Corporation, Waltham, MA (US); Dana-Farber Cancer Institute, Inc., Boston, MA (US)

(*) Notice: Subject to any disclaimer, the term of this patent is extended or adjusted under 35 U.S.C. 154(b) by 1023 days.

(21) Appl. No.: 10/577,003

(22) PCT Filed: Oct. 21, 2004

(86) PCT No.: PCT/US2004/034680
§ 371 (c)(1),
(2), (4) Date: Dec. 13, 2006

(87) PCT Pub. No.: WO2005/042573
PCT Pub. Date: May 12, 2005

(65) Prior Publication Data
US 2007/0105767 A1    May 10, 2007

Related U.S. Application Data

(60) Provisional application No. 60/514,198, filed on Oct. 24, 2003, provisional application No. 60/519,822, filed on Nov. 12, 2003.

(51) Int. Cl.
C07K 1/00 (2006.01)
C07K 14/00 (2006.01)
C07K 17/00 (2006.01)
C07K 16/00 (2006.01)
C12P 21/08 (2006.01)
A61K 39/00 (2006.01)

(52) U.S. Cl. ............ 530/395; 530/362; 530/387.3; 530/387.7; 424/192.1

(58) Field of Classification Search .................. None
See application file for complete search history.

(56) References Cited

U.S. PATENT DOCUMENTS

| | | | |
|---|---|---|---|
| 4,497,796 A | 2/1985 | Salser et al. | 514/44 |
| 4,675,382 A | 6/1987 | Murphy | 260/112 |
| 4,894,227 A | 1/1990 | Stevens et al. | 424/85.2 |
| 4,963,484 A | 10/1990 | Kufe | 435/69.3 |
| 5,053,489 A | 10/1991 | Kufe | 530/350 |
| 5,080,898 A | 1/1992 | Murphy | 424/94.1 |
| 5,116,964 A * | 5/1992 | Capon et al. | |
| 5,380,712 A | 1/1995 | Ballance et al. | 514/12 |
| 5,506,343 A | 4/1996 | Kufe | 530/387.7 |
| 5,530,101 A | 6/1996 | Queen et al. | 530/387.3 |
| 5,565,334 A | 10/1996 | Kufe et al. | 435/69.1 |
| 5,612,895 A | 3/1997 | Balaji et al. | 702/19 |
| 5,766,883 A | 6/1998 | Ballance et al. | 435/69.7 |
| 5,776,427 A | 7/1998 | Thorpe et al. | 424/1.49 |
| 5,801,154 A | 9/1998 | Baracchini et al. | 514/44 |
| 5,861,381 A | 1/1999 | Chambon et al. | 514/44 |
| 5,965,386 A | 10/1999 | Kerry-Williams et al. | 435/69.1 |
| 5,998,148 A | 12/1999 | Bennett et al. | 435/6 |
| 6,004,746 A | 12/1999 | Brent et al. | 435/6 |
| 6,020,363 A | 2/2000 | Hirano et al. | 514/456 |
| 6,054,438 A | 4/2000 | Taylor-Papadimitiou et al. | 514/44 |
| 6,074,841 A | 6/2000 | Gearing et al. | 435/69.1 |
| 6,222,020 B1 | 4/2001 | Taylor-Papadimitiou et al. | 530/395 |
| 6,589,921 B2 | 7/2003 | Herrmann et al. | 514/456 |
| 6,716,627 B2 | 4/2004 | Dobie et al. | 514/44 |
| 2002/0110841 A1 | 8/2002 | Kufe | 435/7.23 |
| 2004/0018181 A1 | 1/2004 | Kufe et al. | 424/93.21 |
| 2004/0166543 A1 | 8/2004 | Kufe | 435/7.23 |
| 2004/0209832 A1 | 10/2004 | McSwiggen | 514/44 |
| 2005/0019324 A1 * | 1/2005 | Wreschner et al. | 424/143.1 |
| 2005/0042209 A1 | 2/2005 | Kufe et al. | 424/93.21 |
| 2005/0053606 A1 | 3/2005 | Kufe et al. | 424/155.1 |
| 2008/0090770 A1 | 4/2008 | Belmares et al. | 514/18 |

FOREIGN PATENT DOCUMENTS

| | | |
|---|---|---|
| EP | 1103623 | 7/1998 |
| WO | WO 93/20841 | 10/1993 |
| WO | WO 96/03502 | 2/1996 |
| WO | WO 99/23114 | 5/1999 |
| WO | WO 91/09867 | 7/1999 |
| WO | WO 00/25827 | 5/2000 |
| WO | WO 00/34468 | 6/2000 |
| WO | WO 00/77031 | 12/2000 |
| WO | WO 01/12217 | 2/2001 |
| WO | WO 01/18035 | 3/2001 |
| WO | WO 01/57068 | 8/2001 |
| WO | WO 02/22685 | 3/2002 |
| WO | WO 02/31512 | 4/2002 |
| WO | WO 02/058450 | 8/2002 |
| WO | WO 03/014303 | 2/2003 |
| WO | WO 03/088995 | 10/2003 |
| WO | WO 03089451 A2 * | 10/2003 |
| WO | WO 2004/015057 A2 * | 2/2004 |
| WO | WO 2004/044160 | 5/2004 |
| WO | WO 2004/092339 | 10/2004 |

OTHER PUBLICATIONS

U.S. Appl. No. 60/308,307, filed Jul. 27, 2001, Kufe.
U.S. Appl. No. 60/502,111, filed Sep. 11, 2003, Jecminek et al.
Abe et al., "Sodium butyrate induction of milk-related antigens in human MCF-7 breast carcinoma cells," *Cancer Res.*, 44:4574-4577, 1984. Adams and Cory, "The Bcl-2 Protein Family: Arbiters of Cell Survival," *Science*, 281:1322-1326, 1998.
Agrawal and Kandimalla, "Antisense therapeutics: is it as simple as complementary base recognition?" *Molecular Medicine Today*, 6:72-81, 2000.
Akagi et al., "CA19-9 epitope a possible marker for MUC-1/Y protein," *Int. J. Oncol.*, 18:1085-1091, 2001.
Apostolopoulos et al., "Production of anti-breast cancer monoclonal antibodies using a glutathione-S-transferase-MUC1 bacterial fusion protein," *British J. Cancer.*, 67:713-720, 1993.
Arklie et al., "Differentiation antigens expressed by epithelial cells in the lactating breast are also detectable in breast cancers," *Int. J. Cancer*, 28:23-29, 1981.
Ashkenazi and Dixit, "Apoptosis control by death and decoy receptors," *Curr. Opin. Cell Biol.*, 11:255-260, 1999.
Ashkenazi and Dixit, "Death Receptors: Signaling and Modulation," *Science*, 281:1305-1308, 1998.
Ashkenazi et al., "Safety and antitumor activity of recombinant soluble Apo2 ligand," *J. Clin. Invest.*, 104:155-162, 1999.
Banerjee, "Omega amino acids in peptide design: incorporation into helices ," *Biopolymers*, 39:769-77, 1996.

(Continued)

*Primary Examiner* — Anne M. Gussow
(74) *Attorney, Agent, or Firm* — Fulbright & Jaworski

(57) ABSTRACT

The present invention provides for chimeric proteins comprising a MUC1 extracellular (MUC1-EC) polypeptide and a carrier polypeptide that function as traps for MUC1 ligands.

14 Claims, No Drawings

OTHER PUBLICATIONS

Barry and Sharkey, "Observer reproducibility during computer-assisted planimetric measurements of nuclear features," *Hum. Pathol.*, 16:225-7, 1985.
Barry et al., "Activation of programmed cell death (apoptosis) by cisplatin, other anticancer drugs, toxins and hyperthermia," *Biochemical Pharmacology*, 40:2353-2362, 1990.
Baruch et al., "The breast cancer-associated MUC1 gene generates both a receptor and its cognate binding protein," *Cancer Res.*, 59:1552-1561, 1999.
Bass, "The short answer," *Nature*, 411:428-429, 2001.
Batra et al., "Transfection of the human MUC1 mucin gene into a poorly differentiated human pancreatic tumor cell line, Panc1: integration, expression and ultrastructural changes," *J. Cell Science*, 100:841-849, 1991.
Bellgrau et al., "A role for CD95 ligand in preventing graft rejection," *Nature*, 377:630-632, 1995.
Berger et al., "Respiratory carcinoma cell lines: MUC genes and glycoconjugates," *American Journal of Respiratory Cell and Molecular Biology*, 20:500-510, 1999.
Bergeron et al., "MAUB is a new mucin antigen associated with bladder cancer," *J. Biol. Chem.*, 271:6933-6940, 1996.
Beusen et al., "Conformational mimicry: synthesis and solution conformation of a cyclic somatostatin hexapeptide containing a tetrazole cis amide bond surrogate," *Biopolymers*, 36:181-200, 1995.
Bird et al., "Single-chain antigen-binding proteins," *Science*, 242:423-6, 1988.
Bitko et al., "Inhibition of respiratory viruses by nasally administered siRNA," *Nature Med.*, 11:50-55, 2005.
Bodmer et al., "Cysteine 230 is essential for the structure and activity of the cytotoxic ligand TRAIL," *J. Biol. Chem.*, 275:20632-20637, 2000.
Boldin et al., "Involvement of MACH, a novel MORT1/FADD-interacting protease, in Fas/APO-1- and TNF receptor-induced cell death," *Cell*, 85:803-815, 1996.
Brossart et al., "Identification of HLA-A2-restricted T-cell epitopes derived from MUC1 tumor antigen for broadly applicable vaccine therapies," *Blood*, 93:4309-4317, 1999.
Brunner et al, "*pangolin* encodes a Lef-1 homologue that acts downstream of Armadillo to transduce the Wingless signal in *Drosophila*," *Nature*, 385:829-33, 1997.
Bumcrot et al., "RNAi therapeutics: a potential new class of pharmaceutical drugs," *Nature Chemical Biology*, 2:711-719, 2006.
Bunz, "Cell death and cancer therapy," *Curr. Opin. Pharmacol.*, 1:337-341, 2001.
Burchell et al., "A short sequence, within the amino acid tandem repeat of a cancer-associated mucin, contains immunodominant epitopes," *Int. J. Cancer*, 44:691-696, 1989.
Burchell et al., "Development and characterization of breast cancer reactive monoclonal antibodies directed to the core protein of the human milk mucin," *Cancer Res.*, 47:5476-5482, 1987.
Burns and El-Deiry, "Identification of inhibitors of TRAIL-induced death (ITIDs) in the TRAIL-sensitive colon carcinoma cell line SW480 using a genetic approach," *J. Biol. Chem.*, 276:37879-37886, 2001.
Burton et al., "Epithelial mucin (MUC1) expression and MA5 anti-MUC1 monoclonal antibody targeting in multiple myeloma," *Clin. Can. Res.*, 5:3065s-3072s, 1999.
Busfield et al., "Characterization of a neuregulin-related gene, *Don-1*, that is highly expressed in restricted regions of the cerebellum and hippocampus," *Mol. Cell. Biol.*, 17:4007-4014, 1997.
Cawley et al., "Epidermal growth factor-toxin A chain conjugates: EGF-Ricin A is a potent toxin while EGF-Diphtheria fragment A is nontoxic," *Cell*, 22:563-570, 1980.
Chang et al., "Artificial hybrid protein containing a toxic protein fragment and a cell membrane receptor-binding moiety in a disulfide conjugate," *J. Biol. Chem.*, 252:1515-1522, 1977.
Chang et al., "Ligands for ErbB-family receptors encoded by a neuregulin-like gene," *Nature*, 387:509-512, 1997.
Chaudhary et al., "A rapid method of cloning functional variable-region antibody genes in *Escherichia coli* as single-chain immunotoxins," *Proc. Natl. Acad. Sci. U.S.A.*, 87:1066-70, 1990.
Chaudhary et al., "Activity of a recombinant fusion protein between transforming growth factor type alpha and *Pseudomonas* toxin," *Proc. Natl. Acad. Sci. USA*, 84:4538-4542, 1987.
Ciborowski et al., "Screening of anti-MUC1 antibodies for reactivity with native (ascites) and recombinant (baculovirus) MUC1 and for blocking MUC1 specific cytotoxic T-lymphocytes," *Tumor Biology*, 19:147-151, 1998.
Console et al., "Antennapedia and HIV transactivator of transcription (TAT) "protein transduction domains" promote endocytosis of high molecular weight cargo upon binding to cell surface glycosaminoglycans," *J. Biol. Chem.*, 278:35109-14, 2003.
Creagan et al., "Phase III clinical trial of the combination of cisplatin, dacarbazine, and carmustine with or without tamoxifen in patients with advanced malignant melanoma," *J. Clin. Oncol.*, 17:1884-1890, 1999.
Croghan et al., "Tissue distribution of an epithelial and tumor-associated antigen recognized by monoclonal antibody F36/22," *Cancer Res.*, 43:4980-4988, 1983.
Daniel and Reynolds, "The catenin p120(ctn) interacts with Kaiso, a novel BTB/POZ domain zinc finger transcription factor," *Mol. Cell. Biol.*, 19:3614-23, 1999.
Datta et al., "Overexpression of Bcl-XL by cytotoxic drug exposure confers resistance to ionizing radiation-induced internucleosomal DNA fragmentation," *Cell Growth Differ*, 6:363-370, 1995.
Dawson et al., "Synthesis of proteins by native chemical ligation ," *Science*, 266:776-779, 1994.
Deng et al., "TRAIL-induced apoptosis requires Bax-dependent mitochondrial release of Smac/DIABLO," *Genes Dev.*, 16:33-45, 2002.
Derossi et al., "Cell internalization of the third helix of the Antennapedia homeodomain is receptor-independent," *J Biol. Chem.*, 271:18188-93, 1996.
Derossi et al., "The third helix of the Antennapedia homeodomain translocates through biological membranes," *J Biol. Chem.*, 269:10444-50, 1994.
Deveraux and Reed, "IAP family proteins—suppressors of apoptosis," *Genes Dev.*, 13:239-52, 1999.
Dillman, "Antibodies as cytotoxic therapy," *J. Clin. Oncology*, 12:1497-1515, 1994.
Dorn et al., "Down-regulation of the human tumor antigen mucin by gemcitabine on the pancreatic cancer cell line capan-2," *Anticancer Research*, 24:821-826, 2004.
Doyle, "Crystal structures of a complexed and peptide-free membrane protein-binding domain: molecular basis of peptide recognition by PDZ," *Cell*, 85:1067-76, 1996.
Drucker et al., "Tamoxifen enhances apoptotic effect of cisplatin on primary endometrial cell cultures," *Anticancer Research*, 23:1549-1554, 2003.
Du et al., "Smac, a Mitochondrial Protein that Promotes Cytochrome c-Dependent Caspase Activation by Eliminating IAP Inhibition," *Cell*, 102:33-42, 2000.
Dykxhoorn et al., "The silent treatment: siRNAs as small molecule drugs," *Gene Therapy*, 13:541-552, 2006.
Elbashir et al., "Functional anatomy of siRNAs for mediating efficient RNAi in *Drosophila melanogaster* embryo lysate," *EMBO Journal*, 20:6877-6888, 2001.
Elbashir et al., "RNA interference is mediated by 21-and 22-nucleotide RNAs," *Genes and Development*, 15:188-200, 2001.
Elliot and O'Hare, "Intercellular trafficking and protein delivery by a herpesvirus structural protein," *Cell*, 88:223-33, 1997.
Elmquist et al., "VE-cadherin-derived cell-penetrating peptide, pVEC, with carrier functions," *Exp. Cell Res.*, 269:237-44, 2001.
Emoto et al., "Proteolytic activation of protein kinase C delta by an ICE-like protease in apoptotic cells," *EMBO J.*, 14:6148-6156, 1995.
Faivre et al., "Supraadditive effect of 2',2'difluorodeoxycytidine (gemcitabine) in combination with oxaliplatin in human cancer cell lines," *Cancer Chemother. Pharmacol.*, 44:117-123, 1999.
Feigl, "2,8-Dimethyl-4-(carboxymethyl)-6-(aminomethyl)phenoxathiin S-Dioxide: An Organic Substitute for the beta-Turn in Peptides," *J. Amer. Chem. Soc.*, 108:181-2, 1986.
Finn et al., "MUC-1 Epithelial Tumor Mucin-Based Immunity and Cancer Vaccines," *Immunol. Rev.*, 145:61-89, 1995.

Fontenot et al., "Biophysical characterization of one-, two-, and three-tandem repeats of human musin (muc-1) protein core," *Cancer Research*, 53:5386-5394, 1993.

Frankel and Pabo, "Cellular uptake of the tat protein from human immunodeficiency virus ," *Cell*, 55:1189-93, 1989.

French and Tschopp, "Inhibition of Death Receptor Signaling by FLICE-inhibitory Protein as a Mechanism for Immune Escape of Tumors," *J. Exp. Med.*, 190:891-893, 1999.

Futaki et al., "Arginine-rich peptides. An abundant source of membrane-permeable peptides having potential as carriers for intracellular protein delivery," *J. Biol. Chem.*, 276 :5836-40, 2001.

Gay et al., "Selective GRB2 SH2 inhibitors as anti-RAS therapy," *Int. J. Cancer*, 83:235-241, 1999.

Geisbert et al., "Postexposure Protection of Guinea Pigs against a Lethal Ebola Virus Challenge is Conferred by RNA Interference," *J. Infectious Diseases*, 193:1650-1657, 2006.

Gendler et al., "Molecular cloning and expression of human tumor-associated polymorphic epithelial mucin," *J. Biol. Chem.*, 265:15286-15293, 1990.

George, D.G. et al., "Chapter 12. Current Methods in Sequence Comparison and Analysis," in: *Macromolecular Sequencing and Synthesis. Selected Methods and Applications*, Alan R. Liss, Inc., pp. 127-149 (1988).

Gopalakrishnan et al., "Application of Micro Arrayed Compound Screening (microARCS) to identify inhibitors of caspase-3," *J. Biomol. Screen*, 7:317-23, 2002.

Green and Loewenstein, "Autonomous functional domains of chemically synthesized human immunodeficiency virus tat trans-activator protein ," *Cell*, 55:1179-88, 1989.

Griffith et al., "CD95-Induced Apoptosis of Lymphocytes in an Immune Privileged Site Induces Immunological Tolerance," *Immunity*, 5:7-16, 1996.

Gross et al., "Caspase cleaved BID targets mitochondria and is required for cytochrome c release, while BCL-XL prevents this release but not tumor necrosis factor-R1/Fas death," *J. Biol. Chem.*, 274:1156-1163, 1999.

Grzelinski et al., "RNA interference-mediated gene silencing of pleiotrophin through polyethylenimine-complexed small interfering RNAs in vivo exerts antitumoral effects in glioblastoma xenografts," *Human Gene Therapy*, 17:751-766, 2006.

Gutierrez et al., "Gene therapy for cancer," *The Lancet*, 339:715-721, 1992.

Haim et al., "Dexamethasone, cytarabine, ifosfamide, and cisplatin as salvage therapy in Non-Hodgkin lymphoma," *Am. J. Clin. Oncol.*, 22:47-50, 1999.

Hammond et al., "Post-transcriptional gene silencing by double-stranded RNA," *Nature Genetics*, 2:110-119, 2001.

Hanson et al.,"MUC1 expression in primary breast cancer: the effect of tamoxifen treatment," *Breast Cancer Research and Treatment*, 67:215-222, 2001.

Harborth et al., "Identification of essential genes in cultured mammalian cells using small interfering RNAs," *J. Cell Science*, 114:4557-4565, 2001.

Harlow and Lane, "Antibodies, A Lab Manual," Cold Spring Harbor, 1988.

Harris et al., "Therapeutic antibodies—the coming of age," *Tibtech*, 11:12-44, 1993.

Harrison, "Peptide-surface association: the case of PDZ and PTB domains," *Cell*, 86:341-343, 1996.

Hartman et al.,"MUC1 isoform specific monoclonal antibody 6E6/2 detects preferential expression of the novel MUC1/Y protein in breast and ovarian cancer," *Int. J. Cancer*, 82:256-267, 1999.

Hayes et al., "Comparison of circulating CA15-3 and carcinembryonic antigen levels in patients with breast cancer," *J. Clin. Oncol.*, 4:1542-1550, 1986.

Hayes et al., "Genetically determined polymorphism of the circulating human breast cancer-associated DF3 antigen," *Blood*, 71:436-440, 1998.

Herr and Debatin, "Cellular stress response and apoptosis in cancer therapy," *Blood*, 98:2603-2614, 2001.

Higashiyama et al., "A novel brain-derived member of the epidermal growth factor family that interacts with ErbB3 and ErbB4," *J. Biochem.*, 122:675-680, 1997.

Higgins, "Comparison of the solution conformations of a human immunodeficiency virus peptidomimetic and its retro-inverso isomer using 1H NMR spectroscopy," *J. Pept. Res.*, 50:421-35, 1997.

Hilkens et al., "Biosynthesis of MAM-6, an epithelial sialomucin," *J. Biol. Chem.*, 263:4215-4222, 1988.

Hilkens et al., "Complexity of MAM-6, an epithelial sialomucin associated with carcinomas," *Cancer Res.*, 49:786-793, 1989.

Hilkens et al., "Monoclonal antibodies against human milk-fat globulte membranes detecting differentiation antigens of the mammary gland and its tumors," *Int. J. Cancer*, 34:197-206, 1984.

Hird et al., "Adjuvant therapy of ovarian cancer with radioactive monoclonal antibody," *Br. J. Cancer*, 68:403-406, 1993.

Hopp, "Protein surface analysis. Methods for identifying antigenic determinants and other interaction sites," *J. Immunol. Methods*, 88:1-18, 1986.

Houghton et al., "Monoclonal antibodies: potential applications to the treatment of cancer," *Seminars in Oncology*, 13:165-179, 1986.

Hruby et al., "Design of peptides, proteins, and peptidomimetics in chi space," *Biopolymers*, 43:219-66, 1997.

Hug et al., "Liposomes for the transformation of eukaryotic cells," *Biochem. Biophys. Acta.*, 1097:1-17, 1991.

Hull et al., "Oligosaccharide differences in the DF3 sialomucin antigen from normal human milk and the BT-20 human breast carcinomas cell line," *Cancer Commun.*, 1:261-267, 1989.

Hunt and Evans, "Till Death Us Do Part," *Science*, 293:1784-1785, 2001.

Huston et al., "Protein engineering of antibody binding sites: recovery of specific activity in an anti-digoxin single-chain Fv analogue produced in *Escherichia coli*," *Proc. Natl. Acad. Sci U.S.A.*, 85:5879-83, 1988.

Hymowitz et al., "Triggering cell death: the crystal structure of Apo2L/TRAIL in a complex with death receptor 5," *Mol. Cell.*, 4:563-571, 1999.

Ikeda et al., "Induction of redox imbalance and apoptosis in multiple myeloma cells by the novel triterpenoid 2-cyano-3, 12-dioxoolean-1, 9-dien-28-oic acid," *Molecular Cancer Therapeutics*, 3:39-45, 2004.

Irmler et al., "Inhibition of death receptor signals by cellular FLIP," *Nature*, 388:190-195, 1997.

Itzkowitz et al., "Sialosyl-Tn. A novel mucin antigen associated with prognosis in colorectal cancer patients," *Cancer*, 66:1960-6, 1990.

Jaattela et al., "Bcl-x and Bcl-2 inhibit TNF and Fas-induced apoptosis and activation of phospholipase A2 in breast carcinoma cells," *Oncogene*, 10:2297-2305, 1995.

Jawhari et al., "Up-regulated cytoplasmic expression, with reduced membranous distribution, of the src substrate p120(ctn) in gastric carcinoma," *J. Pathol.* 189:180-5, 1999.

Jen et al., "Suppression of gene expression by targeted disruption of messenger RNA: available options and current strategies," *Stem Cells*, 18:307-319, 2000.

Jin et al., "CIAP1 and the serine protease HTRA2 are involved in a novel p53-dependent apoptosis pathway in mammals," *Genes Dev.*, 17:359-67, 2003.

Kahn et al., "Nonpeptide Mimetics of beta-Turns: A Facile Oxidative Intramolecular Cycloaddition of an Azodicarbonyl System," *J. Amer. Chem. Soc.*, 110:1638-9, 1988.

Kahn, "The design and synthesis of mimetics of peptide beta-turns," *J. Molec. Recognition*, 1:75-9, 1988.

Kalofonos et al., "Kinetics, quantitative analysis and radioimmunolocalisation using indium-111-HMFG1 monoclonal antibody in patients with breast cancer," *Cr. J. Cancer*, 59:939-942, 1989.

Kalofonos et al., "Radioimmunoschintigraphy in patients with ovarian cancer," *Acta Oncologica*, 38:629-634, 1999.

Kam et al.,"MUC1 synthetic peptide inhibition of intracellular adhesion molecule-1 and MUC1 binding requires six tandem repeats," *Cancer Res.*, 58:5577-5581, 1988.

Karlsson et al., "A genetic polymorphism of a human urinary mucin," *Ann. Hum. Genet.*, 47:263, 1983.

Karvinen et al., "Homogeneous time-resolved fluorescence quenching assay (LANCE) for caspase-3," *J. Biomol. Screen.*, 7:223-31, 2002.

Kataoka et al., "FLIP prevents apoptosis induced by death receptors but not by perforin/granzyme B, chemotherapeutic drugs, and gamma irradiation," *J. Immunol.*, 161:3936-3942, 1998.

Kayagaki et al., "Metalloproteinase-mediated release of human Fas ligand," *J. Exp. Med.*, 182:1777-1783, 1995.

Kemp and Stites, "A convenient preparation of derivatives of 3(s)-amino-109(r)-carboxy-1,6-diaza-cyclodeca-2,7-dione the dilactam of L-alph,gamma-diaminobutyric acid and d-glutamic acid: a beta-turn template," *Tet. Lett.*, 29:5057-60, 1988.

Kennerdell et al., "Heritable gene silencing in *Drosophila* using double-stranded RNA," *Nature Biotechnology*, 17:896-898, 2000.

Kharbanda et al., "Nuclear signaling induced by ionizing radiation involves colocalization of the activated p56/p53lyn tyrosine kinase with p34cdc2," *Cancer Res.*, 56:3617-3621, 1996.

Kim et al., "Cholesteryl oligoarginine delivering vascular endothelial growth factor siRNA effectively inhibits tumor growth in colon adenocarcinoma," *Molecular Therapy*, 14:343-350, 2006.

Kischkel et al., "Cytotoxicity-dependent APO-1 (Fas/CD95)-associated proteins form a death-inducing signaling complex (DISC) with the receptor," *EMBO J.*, 14:5579-5588, 1995.

Kluck et al., "The Release of Cytochrome c from Mitochondria: A Primary Site for BCL-2 Regulation of Apoptosis," *Science*, 275:1132-1136, 1997.

Kondo et al., "Decreased MUC1 expression induces E-Cadherin-mediated cell adhesion of breast cancer cell lines," *Cancer Research*, 58:2014-2019, 1998.

Kotera et al., "Humoral immunity against a tandem repeat epitope of human mucin MUC-1 in Ser from breat, pancreatic, and colon cancer patients," *Cancer Research*, 54:2856-2860, 1994.

Kroemer and Reed, "Mitochondrial control of cell death," *Nat. Med.*, 6:513-519, 2000.

Kumar et al., "Abrogation of the cell death response to oxidative stress by the c-Abl tyrosine kinase inhibitor STI571," *Mol. Pharmacol.*, 63:276-282, 2003.

Kuppuswamy et al., "Multiple functional domains of Tat, the trans-activator of HIV-1, defined by mutational analysis," *Nucl. Acids Res.*, 17:3551-61, 1989.

Lancaster et al., "Structure and expression of the human polymorphic epithelial mucin cenge: an expressed VNTR unit," *Biochm. Biophys. Res. Comm.*, 173:1019-1029, 1990.

LaVallee et al., "2-Methoxyestradiol up-regulates death receptor 5 and induces apoptosis through activation of the extrinsic pathway," *Cancer Research*, 63:468-475, 2003.

LeBlanc et al., "Tumor-cell resistance to death receptor-induced apoptosis through mutational inactivation of the proapoptotic Bcl-2 homolog Bax," *Nat. Med.*, 8:274-281, 2002.

Lewis et al., "Efficient delivery of siRNA for inhibition of gene expression in postnatal mice," *Nature Genetics*, 32:107-108, 2002.

Li and Kufe, "The human DF3/MUC1 carcinoma-associated antigen signals nuclear localization of the catenin p120$^{ctn}$," *Biochem. Biophys. Res. Commun.*, 281:440-443, 2001.

Li et al., "Cleavage of BID by Caspase 8 Mediates the Mitochondrial Damage in the FAS Pathway of Apoptosis," *Cell*, 94:491-501, 1998.

Li et al., "Cytochrome c and dATP-Dependent Formation of Apaf-1 /Caspase-9 Complex initiates and Apoptotic Protease Cascade," *Cell*, 91:479-489, 1997.

Li et al., "DF3/MUC1 signaling in multiple myeloma cells is regulated by interleukin-7," *Cancer Biol. Ther.*, 2:187-193, 2003.

Li et al., "The EGF receptor regulates interaction of the human DF3/MUC1 carcinoma antigen with c-SRC and β-catenin," *JBC Papers in Press*, manuscript C100359200, Aug. 1, 2001.

Li et al., "Using siRNA in prophylactic and therapeutic regimens against SARS coronavirus in Rhesus macaque," *Nature Med.*, 11:944-951, 2005.

Ligtenberg et al., "Cell associated episialin is a complex containing two proteins derived from a common precurso," *J. Biol. Chem.*, 267:6171-6177, 1992.

Lin et al., "Inhibition of nuclear translocation of transcription factor NF-kappa B by a synthetic peptide containing a cell membrane-permeable motif and nuclear localization sequence," *J. Biol. Chem.*, 270:14255-8, 1995.

Liu et al., "Identification of a functionally important sequence in the cytoplasmic tail of integrin beta 3 by using cell-permeable peptide analogs," *Proc. Natl Acad. Sci. U.S.A.*, 93:11819-24, 1996.

Liu et al., "Induction of Apoptotic Program in Cell-Free Extracts: Requirement of dATP and Cyochrome c," *Cell*, 86:147-157, 1996.

Luo et al., "An efficient intrathecal delivery of small interfering RNA to the spinal cord and peripheral neurons," *Molecular Pain*, 1:29, 2005.

Luo et al., "Bid, a Bcl2 Interacting Protein, Mediates Cytochrome c Release from Mitochondria in Response to Activation of Cell Surface Death Receptors," *Cell*, 94:481-490, 1998.

Makimura et al., "Reducing hypothalamic AGRP by RNA interference increases metabolic rate and decreases body weight without influencing food intake," *BMC Neuroscience*, 3:18, 2002.

Maraveyas et al., "Pharmacokinetics and toxicity of an Yttrium-90-CITC-DTPA-HMFG1 radioimmunoconjugate for intraperitoneal radioimmunotherapy of ovarian cancer," *Cancer*, 73:1067-1075, 1994.

Maraveyas et al., "Pharmacokinetics, biodistribution, and dosimetry of specific and control radiolabeled monoclonal antibodies in patients with primary head and neck squamous cell carcinoma," *Cancer Research*, 55:1060-1069, 1995.

Mariani et al., "Regulation of cell surface APO-1/Fas (CD95) ligand expression by metalloproteases," *Eur. J. Immunol.*, 25:2303-2307, 1995.

Marsters et al., "A novel receptor for Apo2L/TRAIL contains a truncated death domain," *Curr. Biol.*, 7:1003-1006, 1997.

Martinez et al., "Single-stranded antisense siRNAs guide target RNA cleavage in RNAi," *Cell*, 110:563-574, 2002.

Martins, "The serine protease Omi/HtrA2: a second mammalian protein with a Reaper-like function," *Cell Death Diff.*, 9:699-701, 2002.

McGrath et al., "The Yeast STE6 gene encodes a homologue of the mammalian mulitdrug resistance P-Glycoprotein," *Nature.*, 340:400, 1989.

McGuckin et al., "Prognostic significance of MUC1 epithelial mucin expression in breast cancer," *Human Pathology*, 26:432-439, 1995.

Melani et al., "Inhibition of proliferation by c-myb antisense oligodeoxynucleoides in colon adenocarcinoma cell lines that express c-myb," *Cancer Research*, 51:2897-2901, 1991.

Mi et al., "Characterization of a class of cationic peptides able to facilitate efficient protein transduction in vitro and in vivo," *Mol. Ther.*, 2:339-47, 2000.

Milik et al., "Lung lymphocyte elimination by apoptosis in the murine response to intratracheal particulate antigen," *J. Clin. Invest.*, 99:1082-1091, 1997.

Minakuchi et al., "Atelocollagen-mediated synthetic small interfering RNA delivery for effective gene silencing in vitro and in vivo," *Nucleic Acids Research*, 32:e109, 2004.

Molenaar et al., XTcf-3 transcription factor mediates beta-catenin-induced axis formation in Xenopus embryos, *Cell*, 86:391-9, 1996.

Morris et al., "A new peptide vector for efficient delivery of oligonucleotides into mammalian cells," *Nucleic Acid Res.*, 25:2730-6, 1997.

Muzio et al., "FLICE, a Novel FADD-Homologous ICE/CED-3-like Protease, Is Recruited to the CD95 (fas/APO-1) Death-Inducing Signaling Complex," *Cell*, 85:817-827, 1996.

Nagai and Sato, "Synthesis of a bicylic dipeptide with the shape of beta-turn central part," *Tet. Lett.*, 26:647-50, 1985.

Nagata, "Apoptosis by Death Factor," *Cell*, 88:355-365, 1997.

Nakamura et al., "RNA interference targeting transforming growth factor-beta type II receptor suppresses ocular inflammation and fibrosis," *Molecular Vision*, 10:703-711, 2004.

Nakashima et al., "Inhibition of angiogenesis by a new isocoumarin, NM-3," *J. Antibiotics*, 52:426-428, 1999.

Neyfakh et al., "Efflux-mediated multidrug resistance in *Bacillus subtilis*: similarities and dissimilarities with the mammalian system," *Proc. Natl. Acad. Sci. USA*, 88:4781-4785, 1991.

Nicholson et al., "Radioimmunotherapy after chemotherapy compared to chemotherapy alone in the treatment of advanced ovarian cancer: a matched analysis," *Oncology Reports* 5:223-226, 1998.

Niethammer et al., "CRIPT, a novel postsynaptic protein that binds to the third PDZ domain of PSD-95/SAP90," *Neuron*, 20:693-707, 1989.

Niu et al., "Inhibition of HPV 16 E6 oncogene expression by RNA interference in vitro and in vivo," *Int. J. Gynecol. Cancer*, 16:743-751, 2006.

Novak and Dedhar, "Signaling through beta-catenin and Lef/Tcf," *Cell Mol. Life Sci.*, 523-37, 1999.

Oehlke et al., "Cellular uptake of an alpha-helical amphipathic model peptide with the potential to deliver polar compounds into the cell interior non-endocytically," *Biochim. Biophys. Acta.*, 1414: 127-39, 1998.

Okazaki et al., "Downregulation of gastric mucin gene expression and its biosynthesis by dexamethasone in the human," *J. Clin. Gastroenterol.*, 27(suppl. 1):S91-S92, 1998.

Opalinska et al., "Nucleic-acid therapeutics: basic principles and recent applications," *Nature Reviews Drug Discovery*, 1:503-514, 2002.

Orkin Report & Recommendations of The Panel to Assess the NIH Investment in Research on Gene Therapy, 1995.

Padrón et al., "Selective cell kill of the combination of gemcitabine and cisplatin in multilayered postconfluent tumor cell cultures," *Anti-Cancer Drugs*, 10:445-452, 1999.

Palliser et al., "An siRNA-based microbicide protects mice from lethal herpes simplex virus 2 infection," *Nature*, 439:89-94, 2006.

Pan et al., "An Antagonist Decoy Receptor and a Death Domain-Containing Receptor for TRAIL," *Science*, 277:815-818, 1997.

Pan et al., "The Receptor for the Cytotoxic Ligand TRAIL," *Science*, 276:111-113, 1997.

Pandey et al., "Association of the DF3/MUC1 breast cancer antigen with Grb2 and the Sos/Ras exchange protein," *Cancer Res.*, 55:4000-4003, 1995.

Parrish et al., "Functional anatomy of a dsRNA trigger: differential requirement for the two trigger strands in RNA interference," *Molecular Cell*, 8:1077-1087, 2000.

Paszkiewicz-Gadek et al., "Biosynthesis of MUC1 mucin in human endometrial adenocarcinoma is modulated by estradiol and tamoxifen," *Gynecol. Endocrinol.*, 17:37-44, 2003.

Pavlovic et al., "Targeting of non-small cell lung cancer using HMFG1-$^{99m}$TC monoclonal antibodies," *Med Pregl.*, 46 Suppl 1:26-28, 1993.

Perey et al., "Tumor selective reactivity of a monoclonal antibody prepared against a recombinant peptide derived from the DF3 human breast carcinoma-associated antigen," *Cancer Research*, 52:2563-2568, 1992.

Perez et al., "Antennapedia homeobox as a signal for the cellular internalization and nuclear addressing of a small exogenous peptide," *J. Cell. Sci.*, 102:717-22, 1992.

Pescarolo et al., "A retro-inverso peptide homologous to helix 1 of c-Myc is a potent and specific inhibitor of proliferation in different cellular systems," *FASEB J.*, 15:31-3, 2001.

Pitti et al., "Induction of Apoptosis by Apo-2 Ligand, a New Member of the Tumor Necrosis Factor Cytokine Family," *J. Biol. Chem.*, 271:12687-12690, 1996.

Pooga et al., "Cell penetrating PNA constructs regulate galanin receptor levels and modify pain transmission in vivo," *Nature Biotech.*, 16 :857-61, 1998.

Porowska et al., "MUC1 expression in human breast cancer cells is altered by the factors affecting cell proliferation," *Neoplasma*, 49:104-109, 2002.

Price et al, "Immunological and structural features of the protein core of human polymorphic epithelial mucin," *Molecular Immunology*, 27:795-802, 1990.

Price et al., "Summary report on the ISOBM TD-4 workshop: analysis of 56 monoclonal antibodies against the MUC1 mucin," San Diego, California, Nov. 17-23, 1996, *Tumor Biol.*, 19:sup. 1:1-20, 1998.

Rewcastle et al., "Tyrosine kinase inhibitors. 14. Structure-activity relationships for methylamino-substituted derivatives of 4-[(3-Bromophenyl) amino]-6-(methylamino)-pyride [3,4-*d*] pyrimidine (PD 158780), a potent and specific inhibitor of the tyrosine kinase activity of receptors for the EGF family of growth factors," *J. Med. Chem.*, 41:742-751, 1998.

Reddish et al., "Pre-immunotherapy serum CA27.29 (MUC-1) mucin level and CD69+ lymphocytes correlate with effects of Theratope sialyl-Tn-KLH cancer vaccine in active specific immunotherapy," *Cancer Immunol. Immunother.*, 42:303-9, 1996.

Reich et al., "Small interfering RNA (siRNA) targeting VEGF effectively inhibits ocular neovascularization in a mouse model," *Molecular Vision*, 9:210-216, 2003.

Reynolds et al., "Identification of a new catenin: the tyrosine kinase substrate p120cas associates with E-cadherin complexes," *Mol. Cell. Biol.*, 14:8333-42, 1994

Reynolds et al., "Transformation-specific tyrosine phosphorylation of a novel cellular protein in chicken cells expressing oncogenic variants of the avian cellular src gene," *Mol. Cell. Biol.*, 9:629-38, 1989.

Rondinone, "Therapeutic potential of rnai in metabolic diseases," *BioTechniques*, 40:S31-S36, 2006.

Rousselle et al., "New advances in the transport of doxorubicin through the blood-brain barrier by a peptide vector-mediated strategy," *Mol. Pharmacol.*, 57 :679-86, 2000.

Ruben et al., "Structural and functional characterization of human immunodeficiency virus tat protein," *J. Virol.*, 63(1):1-8, 1989.

Sato et al., "FAP-1: A Protein Tyrosine Phosphatase That Associates with Fas," *Science*, 268:411-415, 1995.

Scaffidi et al., "Differential Modulation of Apoptosis Sensitivity in CD95 Type I and Type II Cells," *J. Biol. Chem.*, 274:22532-22538, 1999.

Schiffelers et al., "Cancer siRNA therapy by tumor selective delivery with ligand-targeted sterically stabilized nanoparticle," *Nucleic Acids Research*, 32:e149, 2004.

Schneider et al., "Mutagenesis and selection of PDZ domains that bind new protein targets," *Nat. Biotech.*, 17:170-5, 1998.

Schultz et al., "Specific interactions between the syntrophin PDZ domain and voltage-gated sodium channels," *Nat. Struct. Biol.*, 5:19-24, 1998.

Schumacher et al., "Immunoscintigraphy with positron emission tomography: Gallium-68 chelate imaging of breast cancer pretargeted with bispecific anti-MUC1/anti-Ga chelate antibodies," *Cancer Research*, 61:3712-3717, 2001.

Sekine et al., "Purification and characterization of a high molecular weight glycoprotein detectable in human milk and breast carcinomas," *J. Immunol.*, 135:3610-3615, 1985.

Shen et al., "Suppression of ocular neovascularization with siRNA targeting VEGF receptor 1," *Gene Therapy*, 13:225-234, 2006.

Sherman et al., "Ionizing radiation regulates expression of the c-jun protooncogene," *Proc. Natl. Acad. Sci. USA*, 87:5663-5666, 1990.

Shimazui et al., "Prognostic value of cadherin-associated molecules (alpha-, beta-, and gamma-catenins and p120cas) in bladder tumors," *Cancer Res.*, 56:4154-8, 1996.

Sloane et al., Distribution of epithelial membrane antigen in normal and neoplastic tissues and its value in diagnostic tumor pathology, *Cancer*, 47:1786-1795, 1981.

Smith and Waterman, "Comparison of Biosequences," *Adv. Appl. Math.*, 2:482-9, 1981.

Smith, "Design, Synthesis, and Crystal Structure of a Pyrrolinon-Based Peptidomimetic Possessing the Conformation of a beta-Strand: Potential Application to the Design of Novel Inhibitors of Proteolytic Enzymes," *J. Amer. Chem. Soc.*, 114:10672-4, 1992.

Snyder et al., "Treatment of Terminal Peritoneal Carcinomatosis by a Transducible p53-Activating peptide," *PLoS Biology*, 2:186-93, 2004.

Songyang et al., "Recognition of unique carboxyl-terminal motifs by distinct PDZ domains," *Science*, 275:73-7, 1997.

Soomets et al., "Deletion analogues of transportan," *Biochim. Biophys. Acta*, 1467:165-176, 2000.

Soutschek et al., "Therapeutic silencing of an endogenous gene by systemic administration of modified siRNAs," *Nature*, 432:173-178, 2004.

Spatola, "A Peptide Backbone Modifications," In: Chemistry and Biochemistry of Amino Acids, Peptides and Proteins, 7:267-357, Marcell Dekker, NY, 1983.

Srinivasan et al., "Bcl-xL functions downstream of caspase-8 to inhibit Fas- and tumor necrosis factor receptor 1-induced apoptosis of MCF7 breast carcinoma cells," *J. Biol. Chem.*, 273:4523-4529, 1998.

Srinivasula et al., "Autoactivation of procaspase-9 by Apaf-1-mediated oligomerization," *Mol. Cell.*, 1:949-957, 1998.

Stennicke et al., "Pro-caspase-3 is a major physiologic target of caspase-8," *J. Biol. Chem.*, 273:27084-27090, 1998.

Strous and Decker, "Mucin-Type Glycoproteins," *Crit. Rev. Biochem., Mol. Biol.*, 27:57-92, 1992.
Struhl, "Delection mapping a eukaryotic promoter," *Proc. Natl. Acad. Sci. USA*, 78:4461-4465, 1981.
Subbarao et al., "pH-dependent bilayer destabilization by an amphipathic peptide," *Biochemistry*, 26:2964-2972, 1987.
Swallow et al., "The human tumour-associated epithelial mucins are coded by an expressed hypervariable gene locus PUM," *Nature*, 328:82-84, 1987.
Takei et al., "A small interfering RNA targeting vascular endothelial growth factor as cancer therapeutics," *Cancer Research*, 64:3365-3370, 2004.
Takeichi, "Cadherins: a molecular family important in selective cell-cell adhesion," *Annu. Rev. Biochem.*, 59:237-52, 1990.
Taylor et al., "Antisense oligonucleotides: a systematic high-throughput approach to target validation and gene function determination," *Drug Discovery Today*, 4:562-567, 1999.
Thakker et al., "siRNA-mediated knockdown of the serotonin transporter in the adult mouse brain," *Molecular Psychiatry*, 10:782-789, 2005.
Timmer et al., "Fas receptor-mediated apoptosis: a clinical application?" *J. Pathol.*, 196:125-134, 2002.
Tondini et al., "Comparison of CA15-3 and carcinoembryonic antigen in monitoring the clinical course of patients with metastatic breast cancer," *Cancer Res.*, 48:4107-4112, 1988.
Tondini et al., "Evaluation of monoclonal antibody DF3 conjugated with ricin as a specific immunotoxin for in Vitro purging of human bone marrow," *Cancer Research*, 50:1170-1175, 1990.
Topp et al., "MUC-1 specific T-cells are present in multiple myeloma patients at high frequency after allogeneic transplantation buy may not mediated the graft versus myeloma effect," *Blood*, 100: p. Abstract No. 5191, 2002.
Torchilin and Levchenko, "TAT-liposomes: a novel intracellular drug carrier," *Curr. Protein Pept. Sci.*, 4:133-40, 2003.
Tseng et al., "Translocation of liposomes into cancer cells by cell-penetrating peptides penetratin and tat: a kinetic and efficacy study," *Mol. Pharmacol.*, 62:864-72, 2002.
Urban-Klein et al., "RNAi-mediated gene-targeting through systemic application of polyethylenimine (PEI)-complexed siRNA in vivo," *Gene Therapy*, 12:461-466, 2005.
van Hof et al., "Biodistribution of 111Indium-labeled engineered human antibody CTMO1 in ovarian cancer patients: influence of protein dose," *Cancer Research*, 56:5179-5185, 1996.
Van Zonneveld et al., "Type 1 plasminogen activator inhibitor gene: Functional analysis and glucocorticoid regulation of its promoter," *Proc. Natl. Acad. Sci. USA*, 85:5525-5529, 1988.
Verhagen et al., "Identification of DIABLO, a Mammalian Protein that Promotes Apoptosis by Binding to and Antagonizing IAP Proteins," *Cell*, 102:43-53, 2000.
Vermeer et al., "Segregation of receptor and ligand regulates activation of epithelial growth factor receptor," *Nature*, 422:322-326, 2003.
Vives et al., "A truncated HIV-1 Tat protein basic domain rapidly translocates through the plasma membrane and accumulates in the cell nucleus,"*J. Biol. Chem.*, 272 :16010-7, 1997.
Vleck et al., "Pseudorabies virus immediate-early gene overlaps with an oppositely oriented open reading frame: Characterization of their promoter and enhancer regions," *Virology*, 179:365,337, 1990.
Walczak et al., "TRAIL-R2: a novel apoptosis-mediating receptor for TRAIL," *EMBO J.*, 16:5386-5397, 1997.
Walczak et al., "Tumoricidal activity of tumor necrosis factor-related apoptosis-inducing ligand in vivo," *Nat. Med.*, 5:157-163, 1999.
Waldmann, "Monoclonal antibodies in diagnosis and therapy," *Science* 252:1657-1662, 1991.
Walsh et al., "Heterogeneity of MUC1 expression by human breast carcinoma cell lines in vivo and in vitro," *Breast Cancer Research and Treatment*, 58:255-266, 2000.
Wang and El-Deiry, "TRAIL and apoptosis induction by TNF-family death receptors," *Oncogene*, 24:8628-8633, 2003.
Wei et al., "MUC1 oncoprotein stabilizes and activates estrogen receptor α," *Molecular Cell*, 21:295-305, 2006.
Wender et al., "The design, synthesis, and evaluation of molecules that enable or enhance cellular uptake: peptoid molecular transporters," *Proc. Natl. Acad. Sci., U.S.A.*, 97:13003-8, 2000.

Williams et al., "Selective inhibition of growth factor-stimulated mitogenesis by a cell-permeable Grb2-binding peptide,"*J. Biol. Chem.*, 272:22349-54, 1997.
Wreschner et al., "Does a novel form of the breast cancer marker protein MUC1, act as receptor molecule that modulates signal transduction," In: *Antigen and Antibody Molecular Engineering in Breast Cancer Diagnosis and Treatment*, Ed. Ceriani Plenum Press, New York, pp. 17-26, 1994.
Xia et al., "siRNA-mediated gene silencing in vitro and invivo," *Nature Biotechnology*, 20:1006-1010, 2002.
Xing et al, "Synthetic peptides reactive with anti-human milk fat globule membrane monoclonal antibodies," *Cancer Research*, 50:89-96, 1990.
Xing et al., "Effect of variations in peptide sequence on anti-human milk fat globule membrane antibody reactions," *Immunology*, 72:304-311, 1991.
Xing et al., "Epitope mapping of anti-breast and anti-ovarian mucin monoclonal antibodies," *Molecular Immunology*, 29:641-650, 1992.
Xing et al., "Monoclonal antibodies reactive with mucin expressed in breast cancer," *Immunol. Cell. Biol.*, 67:183-195, 1989.
Xing et al., Second generation anti-MUC1 peptide monoclonal antibodies, *Cancer Research*, 52:2310-2317, 1992.
Yang et al., "Prevention of Apoptosis by Bcl-2: Release of Cytochrome c from Mitochondria Blocked," *Science*, 275:1129-1132, 1997.
Zimmerman et al., "RNAi-mediated gene silencing in non-human primates," *Nature*, 441:111-114, 2006.
Zrihan-Licht et al., "Tyrosine phosphorylation of the MUC1 breast cancer membrane proteins: cytokine receptor-like molecules," *FEBS Let.*, 356:130-136, 1994.
"MUC-1/X mucin short variant," GenBank Accession No. AAD10856, dated Jun. 5, 2001.
"MUC-1/Z mucin short variant," GenBank Accession No. AAD10858, dated Jun. 5, 2001.
"Mucin 1 precursor, non-repetitive splice from Y [validated]—human," GenBank Accession No. S48146, dated Apr. 20, 2000.
Backstrom et al., "Recombinant MUC1 mucin with a breast cancer-like O-glycosylation produced in large amounts in Chinese-hamster ovary cells," *Biochemical J.*, 376:677-686, 2003.
Barrett et al., "PLU-1 nuclear protein, which is upregulated in breast cancer, shows restricted expression in normal human adult tissues: a new cancer/testis antigen?," *Int. J. Cancer*, 101:581-588, 2002.
Baruch et al., "Preferential expression of novel MUC1 tumor antigen isoforms in human epithelial tumors and their tumor-potentiating function," *Int. J. Cancer*, 71:741-749, 1997.
Cunningham et al., "Calreticulin binding and other biological activities of survival peptide Y-P30 including effects of systemic treatment of rats," *Exp. Neurol.*, 163:457-468, 2000.
Cunningham et al., "Identification of a survival-promoting peptide in medium conditioned by oxidatively stressed cell lines of nervous system origin," *J. Neurosci.*, 18:7047-7060, 1998.
Cunningham et al., "Identification of the human cDNA for new survival/evasion peptide (DSEP): studies in vitro and in vivo of overexpression by neural cells," *Exp. Neurol.*, 177:32-39, 2002.
Elbashir et al., "Analysis of gene function in somatic mammalian cells using small interfering RNAs," *Methods*, 26:199-213, 2002.
Gendler et al., "A highly immunogenic region of a human polymorphic epithelial mucin expressed by carcinomas is made up of tandem repeats," *J Biol Chem*, 263:12820-12823, 1988.
Julian and Carson, "Formation of MUC1 metabolic complex is conserved in tumor-derived and normal epithelial cells," *Biochem. Biophys. Res. Commun.*, 293:1183-1190, 2002.
Kufe et al., "Differential reactivity of a novel monoclonal antibody (DF3) with human malignant versus benign breast tumors," *Hybridoma*, 3:223-232, 1984.
Li et al., "Heregulin targets gamma-catenin to the nucleolus by a mechanism dependent on the DF3/MUC1 oncoprotein," *Mol Cancer Res*, 1:765-775, 2003.
Li et al., "Human DF3/MUC1 carcinoma-associated protein functions as an oncogene," *Oncogene*, 22:6107-6110, 2003.
Li et al., "Interaction of glycogen synthase kinase 3beta with the DF3/MUC1 carcinoma-associated antigen and beta-catenin," *Mol Cell Biol*, 18:7216-7224, 1998.

Li et al., "The c-Src tyrosine kinase regulates signaling of the human DF3/MUC1 carcinoma-associated antigen with GSK3 beta and beta-catenin," *J Biol Chem*, 276:6061-6064, 2001.

Li et al., "The epidermal growth factor receptor regulates interaction of the human DF3/MUC1 carcinoma antigen with c-Src and beta-catenin," *J Biol Chem*, 276:35239-35242, 2001.

Ligtenberg et al., "Suppression of cellular aggregation by high levels of episialin,"*Cancer Res*, 52:2318-2324, 1992.

Obermair et al., "Expression of MUC1 splice variants in benign and malignant ovarian tumours," *Int. J. Cancer*., 100:166-171, 2002.

Oosterkamp et al., "Comparison of MUC-1 mucin expression in epithelial and non-epithelial cancer cell lines and demonstration of a new short variant form (MUC-1/Z)," *Int. J. Cancer*, 72:87-94, 1997.

Parry et al., "Identification of MUC1 proteolytic cleavage sites in vivo," *Biochem. Biophys. Res. Commun*., 283:715-720, 2001.

Porter et al., "A neural survival factor is a candidate oncogene in breast cancer," *Proc. Natl. Acad. Sci. USA*, 100:10931-10936, 2003.

Ren et al., "Human MUC1 carcinoma-associated protein confers resistance to genotoxic anticancer agents," *Cancer Cell*, 5, 163-175, 2004.

Ren et al., "Protein kinase C delta regulates function of the DF3/MUC1 carcinoma antigen in beta-catenin signaling," *J Biol Chem*, 277:17616-17622, 2002.

Schroeder et al., "Transgenic MUC1 interacts with epidermal growth factor receptor and correlates with mitogen-activated protein kinase activation in the mouse mammary gland," *J Biol Chem*, 276:13057-13064, 2001.

Siddiqui et al, "Isolation and sequencing of a cDNA coding for the human DF3 breast carcinoma-associated antigen," *Proc Natl Acad Sci USA*, 85:2320-2323, 1988.

Yamamoto et al., "Interaction of the DF3/MUC1 breast carcinoma-associated antigen and beta-catenin in cell adhesion," *J Biol Chem*, 272:12492-12494, 1997.

Yeh et al., "Design of yeast-secreted albumin derivatives for human therapy: biological and antiviral properties of a serum albumin-CD4 genetic conjugate," *Proc. Natl. Acad. Sci. USA*, 89:1904-1908, 1992.

Zrihan-Licht et al., "Characterization and molecular cloning of a novel MUC1 protein, devoid of tandem repeats, expressed in human breast cancer tissue," *Eur. J. Biochem*., 224:787-795, 1994.

\* cited by examiner

SEQUENCE LISTING

```
<160> NUMBER OF SEQ ID NOS: 72

<210> SEQ ID NO 1
<211> LENGTH: 164
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30
```

```
Ser Gly His Ala Ser Ser Thr Pro Gly Gly Glu Lys Glu Thr Ser Ala
         35                  40                  45

Thr Gln Arg Ser Ser Val Pro Ser Ser Thr Glu Lys Asn Ala Phe Asn
 50                  55                  60

Ser Ser Leu Glu Asp Pro Ser Thr Asp Tyr Tyr Gln Glu Leu Gln Arg
 65                  70                  75                  80

Asp Ile Ser Glu Met Phe Leu Gln Ile Tyr Lys Gln Gly Gly Phe Leu
                 85                  90                  95

Gly Leu Ser Asn Ile Lys Phe Arg Pro Gly Ser Val Val Gln Leu
            100                 105                 110

Thr Leu Ala Phe Arg Glu Gly Thr Ile Asn Val His Asp Met Glu Thr
            115                 120                 125

Gln Phe Asn Gln Tyr Lys Thr Glu Ala Ala Ser Arg Tyr Asn Leu Thr
        130                 135                 140

Ile Ser Asp Val Ser Val Ser Asp Val Pro Phe Pro Phe Ser Ala Gln
145                 150                 155                 160

Ser Gly Ala Gly

<210> SEQ ID NO 2
<211> LENGTH: 492
<212> TYPE: DNA
<213> ORGANISM: Homo sapiens

<400> SEQUENCE: 2
atgacaccgg gcacccagtc tcctttcttc ctgctgctgc tcctcacagt gcttacagct      60
accacagccc ctaaaccgc  aacagttgtt acaggttctg gtcatgcaag ctctacccca     120
ggtggagaaa aggagacttc ggctacccag agaagttcag tgcccagctc tactgagaag     180
aatgctttta ttcctctct  ggaagatccc agcaccgact actaccaaga gctgcagaga     240
gacatttctg aaatgttttt gcagatttat aaacaagggg gttttctggg cctctccaat     300
attaagttca ggccaggatc tgtggtggta caattgactc tggccttccg agaaggtacc     360
atcaatgtcc acgacatgga gacacagttc aatcagtata aaacggaagc agcctctcga     420
tataacctga cgatctcaga cgtcagcgtg agtgatgtgc catttccttt ctctgcccag     480
tctggggctg gg                                                         492

<210> SEQ ID NO 3
<211> LENGTH: 155
<212> TYPE: PRT
<213> ORGANISM: Homo sapiens

<400> SEQUENCE: 3

Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
             20                  25                  30

Gly Glu Lys Glu Thr Ser Ala Thr Gln Arg Ser Ser Val Pro Ser Ser
         35                  40                  45

Thr Glu Lys Asn Ala Phe Asn Ser Ser Leu Glu Asp Pro Ser Thr Asp
 50                  55                  60

Tyr Tyr Gln Glu Leu Gln Arg Asp Ile Ser Glu Met Phe Leu Gln Ile
 65                  70                  75                  80

Tyr Lys Gln Gly Gly Phe Leu Gly Leu Ser Asn Ile Lys Phe Arg Pro
                 85                  90                  95

Gly Ser Val Val Val Gln Leu Thr Leu Ala Phe Arg Glu Gly Thr Ile
```

```
                  100                 105                 110
Asn Val His Asp Val Glu Thr Gln Phe Asn Gln Tyr Lys Thr Glu Ala
        115                 120                 125

Ala Ser Arg Tyr Asn Leu Thr Ile Ser Asp Val Ser Val Ser Asp Val
        130                 135                 140

Pro Phe Pro Phe Ser Ala Gln Ser Gly Ala Gly
145                 150                 155

<210> SEQ ID NO 4
<211> LENGTH: 465
<212> TYPE: DNA
<213> ORGANISM: Homo sapiens

<400> SEQUENCE: 4
atgacaccgg gcacccagtc tcctttcttc ctgctgctgc tcctcacagt gcttacagtt      60
gttacaggtt ctggtcatgc aagctctacc ccaggtggag aaaaggagac ttcggctacc     120
cagagaagtt cagtgcccag ctctactgag aagaatgctt taattcctc tctggaagat     180 cccagcaccg actactacca agagctgcag agagacattt ctgaaatgtt tttgcagatt     240
tataaacaag ggggttttct gggcctctcc aatattaagt tcaggccagg atctgtggtg     300
gtacaattga ctctggcctt ccgagaaggt accatcaatg tccacgacat ggagacacag     360
ttcaatcagt ataaaacgga agcagcctct cgatataacc tgacgatctc agacgtcagc     420
gtgagtgatg tgccatttcc tttctctgcc cagtctgggg ctggg                    465

<210> SEQ ID NO 5
<211> LENGTH: 173
<212> TYPE: PRT
<213> ORGANISM: Homo sapiens

<400> SEQUENCE: 5

Met Thr Pro Gly Thr Gln Ser Pro Phe Phe Leu Leu Leu Leu Leu Thr
1               5                  10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly
                165                 170

<210> SEQ ID NO 6
<211> LENGTH: 519
<212> TYPE: DNA
```

<213> ORGANISM: Homo sapiens

<400> SEQUENCE: 6

| | |
|---|---|
| atgacaccgg gcacccagtc tccttcttc ctgctgctgc tcctcacagt gcttacagtt | 60 |
| gttacaggtt ctggtcatgc aagctctacc ccaggtggag aaaaggagac ttcggctacc | 120 |
| cagagaagtt cagtgcccag ctctactgag aagaatgctc tgtctactgg ggtctctttc | 180 |
| tttttcctgt cttttcacat ttcaaacctc cagtttaatt cctctctgga agatcccagc | 240 |
| accgactact accaagagct gcagagagac atttctgaaa tgttttgca gatttataaa | 300 |
| caaggggtt ttctgggcct ctccaatatt aagttcaggc caggatctgt ggtggtacaa | 360 |
| ttgactctgg ccttccgaga aggtaccatc aatgtccacg acatggagac acagttcaat | 420 |
| cagtataaaa cggaagcagc ctctcgatat aacctgacga tctcagacgt cagcgtgagt | 480 |
| gatgtgccat ttcctttctc tgcccagtct ggggctggg | 519 |

<210> SEQ ID NO 7
<211> LENGTH: 140
<212> TYPE: PRT
<213> ORGANISM: Homo sapiens

<400> SEQUENCE: 7

```
Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Thr
        35                  40                  45

Asp Tyr Tyr Gln Glu Leu Gln Arg Asp Ile Ser Glu Met Phe Leu Gln
    50                  55                  60

Ile Tyr Lys Gln Gly Gly Phe Leu Gly Leu Ser Asn Ile Lys Phe Arg
65                  70                  75                  80

Pro Gly Ser Val Val Val Gln Leu Thr Leu Ala Phe Arg Glu Gly Thr
                85                  90                  95

Ile Asn Val His Asp Val Glu Thr Gln Phe Asn Gln Tyr Lys Thr Glu
            100                 105                 110

Ala Ala Ser Arg Tyr Asn Leu Thr Ile Ser Asp Val Ser Val Ser Asp
        115                 120                 125

Val Pro Phe Pro Phe Ser Ala Gln Ser Gly Ala Gly
    130                 135                 140
```

<210> SEQ ID NO 8
<211> LENGTH: 420
<212> TYPE: DNA
<213> ORGANISM: Homo sapiens

<400> SEQUENCE: 8

| | |
|---|---|
| atgacaccgg gcacccagtc tccttcttc ctgctgctgc tcctcacagt gcttacagtt | 60 |
| gttacaggtt ctggtcatgc aagctctacc ccaggtggag aaaaggagac ttcggctacc | 120 |
| cagagaagtt cagtgcccag caccgactac taccaagagc tgcagagaga catttctgaa | 180 |
| atgttttgc agatttataa acaaggggt ttctgggcc tctccaatat taagttcagg | 240 |
| ccaggatctg tggtggtaca attgactctg gccttccgag aaggtaccat caatgtccac | 300 |
| gacatggaga cacagttcaa tcagtataaa acggaagcag cctctcgata aacctgacg | 360 |
| atctcagacg tcagcgtgag tgatgtgcca tttcctttct ctgcccagtc tggggctggg | 420 |

```
<210> SEQ ID NO 9
<211> LENGTH: 130
<212> TYPE: PRT
<213> ORGANISM: Homo sapiens

<400> SEQUENCE: 9

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Ile Pro Ala Pro Thr Thr Thr Lys Ser Cys Arg
    50                  55                  60

Glu Thr Phe Leu Lys Trp Pro Gly Ser Val Val Gln Leu Thr Leu
65                  70                  75                  80

Ala Phe Arg Glu Gly Thr Ile Asn Val His Asp Val Glu Thr Gln Phe
                85                  90                  95

Asn Gln Tyr Lys Thr Glu Ala Ala Ser Arg Tyr Asn Leu Thr Ile Ser
            100                 105                 110

Asp Val Ser Val Ser Asp Val Pro Phe Pro Phe Ser Ala Gln Ser Gly
        115                 120                 125

Ala Gly
    130

<210> SEQ ID NO 10
<211> LENGTH: 390
<212> TYPE: DNA
<213> ORGANISM: Homo sapiens

<400> SEQUENCE: 10
atgacaccgg gcacccagtc tccttttctt ctgctgctgc tcctcacagt gcttacagtt      60
gttacaggtt ctggtcatgc aagctctacc ccaggtggag aaaaggagac ttcggctacc     120
cagagaagtt cagtgcccag ctctactgag aagaatgcta tcccagcacc gactactacc     180
aagagctgca gagagacatt tctgaaatgg ccaggatctg tggtggtaca attgactctg     240
gccttccgag aaggtaccat caatgtccac gacatggaga cacagttcaa tcagtataaa     300
acggaagcag cctctcgata taacctgacg atctcagacg tcagcgtgag tgatgtgcca     360
tttcctttct ctgcccagtc tggggctggg                                       390

<210> SEQ ID NO 11
<211> LENGTH: 102
<212> TYPE: PRT
<213> ORGANISM: Homo sapiens

<400> SEQUENCE: 11

Phe Asn Ser Ser Leu Glu Asp Pro Ser Thr Asp Tyr Tyr Gln Glu Leu
1               5                   10                  15

Gln Arg Asp Ile Ser Glu Met Phe Leu Gln Ile Tyr Lys Gln Gly Gly
            20                  25                  30

Phe Leu Gly Leu Ser Asn Ile Lys Phe Arg Pro Gly Ser Val Val Val
        35                  40                  45

Gln Leu Thr Leu Ala Phe Arg Glu Gly Thr Ile Asn Val His Asp Val
    50                  55                  60

Glu Thr Gln Phe Asn Gln Tyr Lys Thr Glu Ala Ala Ser Arg Tyr Asn
65                  70                  75                  80

Leu Thr Ile Ser Asp Val Ser Val Ser Asp Val Pro Phe Pro Phe Ser
```

Ala Gln Ser Gly Ala Gly
            100

<210> SEQ ID NO 12
<211> LENGTH: 306
<212> TYPE: DNA
<213> ORGANISM: Homo sapiens

<400> SEQUENCE: 12
tttaattcct ctctggaaga tcccagcacc gactactacc aagagctgca gagagacatt      60
tctgaaatgt ttttgcagat ttataaacaa gggggttttc tgggcctctc caatattaag     120
ttcaggccag gatctgtggt ggtacaattg actctggcct tccgagaagg taccatcaat     180
gtccacgaca tggagacaca gttcaatcag tataaaacgg aagcagcctc tcgatataac     240
ctgacgatct cagacgtcag cgtgagtgat gtgccatttc ctttctctgc ccagtctggg     300
gctggg                                                                306

<210> SEQ ID NO 13
<211> LENGTH: 375
<212> TYPE: PRT
<213> ORGANISM: Homo sapiens

<400> SEQUENCE: 13

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

| | | | | | | | | | | | |
|---|---|---|---|---|---|---|---|---|---|---|---|
| Ser | Thr | Gly | Val | Ser | Phe | Phe | Leu | Ser | Phe | His | Ile | Ser | Asn | Leu |
| | | 260 | | | | 265 | | | | 270 | |

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
        290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
            325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly
        370                 375

<210> SEQ ID NO 14
<211> LENGTH: 1125
<212> TYPE: DNA
<213> ORGANISM: Homo sapiens

<400> SEQUENCE: 14

```
atgacaccgg gcacccagtc tcctttcttc ctgctgctgc tcctcacagt gcttacagtt      60
gttacaggtt ctggtcatgc aagctctacc ccaggtggag aaaaggagac ttcggctacc     120
cagagaagtt cagtgcccag ctctactgag aagaatgctg tgagtatgac cagcagcgta     180
ctctccagcc acagcccggt tcaggctcc tccaccactc agggacagga tgtcactctg     240
gccccggcca cggaaccagc ttcaggttca gctgccacct ggggacagga tgtcacctcg     300
gtcccagtca ccaggccagc cctgggctcc accaccccgc cagccacga tgtcacctca     360
gccccggaca caagccagc ccgggctcc accgccccc cagcccacgg tgtcacctcg     420
gccccggaca ccaggccggc cccgggctcc accgccccc cagcccatgg tgtcacctcg     480
gccccggaca caggcccgc cttgggctcc accgcccctc cagtccacaa tgtcacctcg     540
gcctcaggct ctgcatcagg ctcagcttct actctggtgc acaacggcac ctctgccagg     600
gctaccacaa ccccagccag caagagcact ccattctcaa ttcccagcca ccactctgat     660
actcctacca cccttgccag ccatagcacc aagactgatg ccagtagcac tcaccatagc     720
acggtacctc ctctcacctc ctccaatcac agcacttctc cccagttgtc tactggggtc     780
tcttctctt tcctgtcttt tcacatttca aacctccagt ttaattcctc tctggaagat     840
cccagcaccg actactacca agagctgcag agagacattt ctgaaatgtt tttgcagatt     900
tataaacaag ggggttttct gggcctctcc aatattaagt tcaggccagg atctgtggtg     960
gtacaattga ctctggcctt ccgagaaggt accatcaatg tccacgacgt ggagacacag    1020
ttcaatcagt ataaaacgga agcagcctct cgatataacc tgacgatctc agacgtcagc    1080
gtgagtgatg tgccattcc tttctctgcc cagtctgggg ctggg                     1125
```

<210> SEQ ID NO 15
<211> LENGTH: 337
<212> TYPE: PRT
<213> ORGANISM: Homo sapiens

<400> SEQUENCE: 15

Met Thr Pro Gly Thr Gln Ser Pro Phe Phe Leu Leu Leu Leu Leu Thr

```
              1               5                  10                 15
Val Leu Thr Val Val Thr Gly Ser Gly His Ala Ser Ser Thr Pro Gly
                    20                 25                 30

Gly Glu Lys Glu Thr Ser Ala Thr Gln Arg Ser Ser Val Pro Ser Ser
                35                 40                 45

Thr Glu Lys Asn Ala Val Ser Met Thr Ser Ser Val Leu Ser Ser His
            50                 55                 60

Ser Pro Gly Ser Gly Ser Ser Thr Gln Gly Gln Asp Val Thr Leu
65                  70                 75                 80

Ala Pro Ala Thr Glu Pro Ala Ser Gly Ser Ala Ala Thr Trp Gly Gln
                    85                 90                 95

Asp Val Thr Ser Val Pro Val Thr Arg Pro Ala Leu Gly Ser Thr Thr
                100                105                110

Pro Pro Ala His Asp Val Thr Ser Ala Pro Asp Asn Lys Asn Arg Pro
                115                120                125

Ala Leu Gly Ser Thr Ala Pro Pro Val His Asn Val Thr Ser Ala Ser
                130                135                140

Gly Ser Ala Ser Gly Ser Ala Ser Thr Leu Val His Asn Gly Thr Ser
145                 150                155                160

Ala Arg Ala Thr Thr Thr Pro Ala Ser Lys Ser Thr Pro Phe Ser Ile
                165                170                175

Pro Ser His His Ser Asp Thr Pro Thr Thr Leu Ala Ser His Ser Thr
                180                185                190

Lys Thr Asp Ala Ser Ser Thr His His Ser Thr Val Pro Pro Leu Thr
                195                200                205

Ser Ser Asn His Ser Thr Ser Pro Gln Leu Ser Thr Gly Val Ser Phe
                210                215                220

Phe Phe Leu Ser Phe His Ile Ser Asn Leu Gln Phe Asn Ser Ser Leu
225                 230                235                240

Glu Asp Pro Ser Thr Asp Tyr Tyr Gln Glu Leu Gln Arg Asp Ile Ser
                245                250                255

Glu Met Phe Leu Gln Ile Tyr Lys Gln Gly Gly Phe Leu Gly Leu Ser
                260                265                270

Asn Ile Lys Phe Arg Pro Gly Ser Val Val Val Gln Leu Thr Leu Ala
                275                280                285

Phe Arg Glu Gly Thr Ile Asn Val His Asp Val Glu Thr Gln Phe Asn
                290                295                300

Gln Tyr Lys Thr Glu Ala Ala Ser Arg Tyr Asn Leu Thr Ile Ser Asp
305                 310                315                320

Val Ser Val Ser Asp Val Pro Phe Pro Phe Ser Ala Gln Ser Gly Ala
                    325                330                335

Gly
```

<210> SEQ ID NO 16
<211> LENGTH: 1011
<212> TYPE: DNA
<213> ORGANISM: Homo sapiens

<400> SEQUENCE: 16

```
atgacaccgg gcacccagtc tcctttcttc ctgctgctgc tcctcacagt gcttacagtt      60
gttacaggtt ctggtcatgc aagctctacc ccaggtggag aaaaggagac ttcggctacc     120
cagagaagtt cagtgcccag ctctactgag aagaatgctg tgagtatgac cagcagcgta     180
ctctccagcc acagccccgg ttcaggctcc tccaccactc agggacagga tgtcactctg     240
```

```
gccccggcca cggaaccagc ttcaggttca gctgccacct ggggacagga tgtcacctcg      300
gtcccagtca ccaggccagc cctgggctcc accaccccgc cagcccacga tgtcacctca      360
gccccggaca acaagaacag gcccgccttg gctccaccg cccctccagt ccacaatgtc       420
acctcggcct caggctctgc atcaggctca gcttctactc tggtgcacaa cggcacctct      480
gccagggcta ccacaacccc agccagcaag agcactccat tctcaattcc agccaccac      540 tctgatactc ctaccaccct tgccagccat agcaccaaga ctgatgccag tagcactcac      600
catagcacgg tacctcctct cacctcctcc aatcacagca cttctcccca gttgtctact      660
ggggtctctt tcttttttcct gtcttttcac atttcaaacc tccagtttaa ttcctctctg     720
gaagatccca gcaccgacta ctaccaagag ctgcagagag acatttctga aatgtttttg      780
cagatttata acaagggggg ttttctgggc ctctccaata ttaagttcag gccaggatct      840
gtggtggtac aattgactct ggccttccga gaaggtacca tcaatgtcca cgacgtggag      900
acacagttca atcagtataa aacggaagca gcctctcgat ataacctgac gatctcagac      960
gtcagcgtga gtgatgtgcc atttcctttc tctgcccagt ctggggctgg g              1011
```

<210> SEQ ID NO 17
<211> LENGTH: 175
<212> TYPE: PRT
<213> ORGANISM: Homo sapiens

<400> SEQUENCE: 17

```
Ala Thr Thr Thr Pro Ala Ser Lys Ser Thr Pro Phe Ser Ile Pro Ser
1               5                   10                  15

His His Ser Asp Thr Pro Thr Thr Leu Ala Ser His Ser Thr Lys Thr
                20                  25                  30

Asp Ala Ser Ser Thr His His Ser Thr Val Pro Leu Thr Ser Ser
            35                  40                  45

Asn His Ser Thr Ser Pro Gln Leu Ser Thr Gly Val Ser Phe Phe
        50                  55                  60

Leu Ser Phe His Ile Ser Asn Leu Gln Phe Asn Ser Ser Leu Glu Asp
65                  70                  75                  80

Pro Ser Thr Asp Tyr Tyr Gln Glu Leu Gln Arg Asp Ile Ser Glu Met
                85                  90                  95

Phe Leu Gln Ile Tyr Lys Gln Gly Gly Phe Leu Gly Leu Ser Asn Ile
            100                 105                 110

Lys Phe Arg Pro Gly Ser Val Val Gln Leu Thr Leu Ala Phe Arg
        115                 120                 125

Glu Gly Thr Ile Asn Val His Asp Val Glu Thr Gln Phe Asn Gln Tyr
130                 135                 140

Lys Thr Glu Ala Ala Ser Arg Tyr Asn Leu Thr Ile Ser Asp Val Ser
145                 150                 155                 160

Val Ser Asp Val Pro Phe Pro Phe Ser Ala Gln Ser Gly Ala Gly
                165                 170                 175
```

<210> SEQ ID NO 18
<211> LENGTH: 525
<212> TYPE: DNA
<213> ORGANISM: Homo sapiens

<400> SEQUENCE: 18

```
gctaccacaa ccccagccag caagagcact ccattctcaa ttcccagcca ccactctgat       60
actcctacca cccttgccag ccatagcacc aagactgatg ccagtagcac tcaccatagc      120
acggtacctc ctctcaccct ctccaatcac agcacttctc cccagttgtc tactggggtc      180
```

```
tctttctttt tcctgtcttt tcacatttca aacctccagt ttaattcctc tctggaagat        240
cccagcaccg actactacca agagctgcag agagacattt ctgaaatgtt tttgcagatt        300
tataaacaag ggggttttct gggcctctcc aatattaagt tcaggccagg atctgtggtg        360
gtacaattga ctctggcctt ccgagaaggt accatcaatg tccacgacgt ggagacacag        420
ttcaatcagt ataaaacgga agcagcctct cgatataacc tgacgatctc agacgtcagc        480
gtgagtgatg tgccatttcc tttctctgcc cagtctgggg ctggg                       525
```

<210> SEQ ID NO 19
<211> LENGTH: 58
<212> TYPE: PRT
<213> ORGANISM: Homo sapiens

<400> SEQUENCE: 19

```
Ser Val Val Gln Leu Thr Leu Ala Phe Arg Glu Gly Thr Ile Asn
 1               5                  10                  15

Val His Asp Val Glu Thr Gln Phe Asn Gln Tyr Lys Thr Glu Ala Ala
             20                  25                  30

Ser Arg Tyr Asn Leu Thr Ile Ser Asp Val Ser Val Ser Asp Val Pro
         35                  40                  45

Phe Pro Phe Ser Ala Gln Ser Gly Ala Gly
     50                  55
```

<210> SEQ ID NO 20
<211> LENGTH: 174
<212> TYPE: DNA
<213> ORGANISM: Homo sapiens

<400> SEQUENCE: 20

```
tctgtggtgg tacaattgac tctggccttc cgagaaggta ccatcaatgt ccacgacatg         60
gagacacagt tcaatcagta taaaacggaa gcagcctctc gatataacct gacgatctca        120
gacgtcagcg tgagtgatgt gccatttcct ttctctgccc agtctggggc tggg              174
```

<210> SEQ ID NO 21
<211> LENGTH: 50
<212> TYPE: PRT
<213> ORGANISM: Homo sapiens

<400> SEQUENCE: 21

```
Ser Val Val Gln Leu Thr Leu Ala Phe Arg Glu Gly Thr Ile Asn
 1               5                  10                  15

Val His Asp Val Glu Thr Gln Phe Asn Gln Tyr Lys Thr Glu Ala Ala
             20                  25                  30

Ser Arg Tyr Asn Leu Thr Ile Ser Asp Val Ser Val Ser Asp Val Pro
         35                  40                  45

Phe Pro
     50
```

<210> SEQ ID NO 22
<211> LENGTH: 150
<212> TYPE: DNA
<213> ORGANISM: Homo sapiens

<400> SEQUENCE: 22

```
tctgtggtgg tacaattgac tctggccttc cgagaaggta ccatcaatgt ccacgacatg         60
gagacacagt tcaatcagta taaaacggaa gcagcctctc gatataacct gacgatctca        120
gacgtcagcg tgagtgatgt gccatttcct                                         150
```

<210> SEQ ID NO 23
<211> LENGTH: 49
<212> TYPE: PRT
<213> ORGANISM: Homo sapiens

<400> SEQUENCE: 23

Phe Arg Glu Gly Thr Ile Asn Val His Asp Val Glu Thr Gln Phe Asn
1               5                   10                  15

Gln Tyr Lys Thr Glu Ala Ala Ser Arg Tyr Asn Leu Thr Ile Ser Asp
            20                  25                  30

Val Ser Val Ser Asp Val Pro Phe Pro Phe Ser Ala Gln Ser Gly Ala
        35                  40                  45

Gly

<210> SEQ ID NO 24
<211> LENGTH: 147
<212> TYPE: DNA
<213> ORGANISM: Homo sapiens

<400> SEQUENCE: 24
ttccgagaag gtaccatcaa tgtccacgac atggagacac agttcaatca gtataaaacg      60
gaagcagcct ctcgatataa cctgacgatc tcagacgtca gcgtgagtga tgtgccattt     120
cctttctctg cccagtctgg ggctggg                                         147

<210> SEQ ID NO 25
<211> LENGTH: 120
<212> TYPE: PRT
<213> ORGANISM: Homo sapiens

<400> SEQUENCE: 25

Leu Ser Thr Gly Val Ser Phe Phe Leu Ser Phe His Ile Ser Asn
1               5                   10                  15

Leu Gln Phe Asn Ser Ser Leu Glu Asp Pro Ser Thr Asp Tyr Tyr Gln
            20                  25                  30

Glu Leu Gln Arg Asp Ile Ser Glu Met Phe Leu Gln Ile Tyr Lys Gln
        35                  40                  45

Gly Gly Phe Leu Gly Leu Ser Asn Ile Lys Phe Arg Pro Gly Ser Val
    50                  55                  60

Val Val Gln Leu Thr Leu Ala Phe Arg Glu Gly Thr Ile Asn Val His
65                  70                  75                  80

Asp Val Glu Thr Gln Phe Asn Gln Tyr Lys Thr Glu Ala Ala Ser Arg
            85                  90                  95

Tyr Asn Leu Thr Ile Ser Asp Val Ser Val Ser Asp Val Pro Phe Pro
            100                 105                 110

Phe Ser Ala Gln Ser Gly Ala Gly
        115                 120

<210> SEQ ID NO 26
<211> LENGTH: 360
<212> TYPE: DNA
<213> ORGANISM: Homo sapiens

<400> SEQUENCE: 26
ctgtctactg gggtctcttt cttttttcctg tcttttcaca tttcaaacct ccagtttaat     60
tcctctctgg aagatcccag caccgactac taccaagagc tgcagagaga catttctgaa    120 atgttttgc agatttataa acaggggggt tttctgggcc tctccaatat taagttcagg     180

```
ccaggatctg tggtggtaca attgactctg gccttccgag aaggtaccat caatgtccac      240
gacatggaga cacagttcaa tcagtataaa acggaagcag cctctcgata taacctgacg      300
atctcagacg tcagcgtgag tgatgtgcca tttcctttct ctgcccagtc tggggctggg      360
```

<210> SEQ ID NO 27
<211> LENGTH: 77
<212> TYPE: PRT
<213> ORGANISM: Homo sapiens

<400> SEQUENCE: 27

```
Ile Pro Ala Pro Thr Thr Thr Lys Ser Cys Arg Glu Thr Phe Leu Lys
1               5                   10                  15

Trp Pro Gly Ser Val Val Gln Leu Thr Leu Ala Phe Arg Glu Gly
            20                  25                  30

Thr Ile Asn Val His Asp Val Glu Thr Gln Phe Asn Gln Tyr Lys Thr
            35                  40                  45

Glu Ala Ala Ser Arg Tyr Asn Leu Thr Ile Ser Asp Val Ser Val Ser
50                  55                  60

Asp Val Pro Phe Pro Phe Ser Ala Gln Ser Gly Ala Gly
65                  70                  75
```

<210> SEQ ID NO 28
<211> LENGTH: 231
<212> TYPE: DNA
<213> ORGANISM: Homo sapiens

<400> SEQUENCE: 28

```
atcccagcac cgactactac caagagctgc agagagacat ttctgaaatg gccaggatct      60
gtggtggtac aattgactct ggccttccga gaaggtacca tcaatgtcca cgacatggag      120
acacagttca atcagtataa acggaagcag cctctcgata taacctgac gatctcagac      180 gtcagcgtga gtgatgtgcc atttcctttc tctgcccagt ctggggctgg g              231
```

<210> SEQ ID NO 29
<211> LENGTH: 112
<212> TYPE: PRT
<213> ORGANISM: Homo sapiens

<400> SEQUENCE: 29

```
Leu Ser Thr Gly Val Ser Phe Phe Phe Leu Ser Phe His Ile Ser Asn
1               5                   10                  15

Leu Gln Phe Asn Ser Ser Leu Glu Asp Pro Ser Thr Tyr Tyr Gln
            20                  25                  30

Glu Leu Gln Arg Asp Ile Ser Glu Met Phe Leu Gln Ile Tyr Lys Gln
            35                  40                  45

Gly Gly Phe Leu Gly Leu Ser Asn Ile Lys Phe Arg Pro Gly Ser Val
50                  55                  60

Val Val Gln Leu Thr Leu Ala Phe Arg Glu Gly Thr Ile Asn Val His
65                  70                  75                  80

Asp Val Glu Thr Gln Phe Asn Gln Tyr Lys Thr Glu Ala Ala Ser Arg
            85                  90                  95

Tyr Asn Leu Thr Ile Ser Asp Val Ser Val Ser Asp Val Pro Phe Pro
            100                 105                 110
```

<210> SEQ ID NO 30
<211> LENGTH: 336
<212> TYPE: DNA
<213> ORGANISM: Homo sapiens -continued

```
<400> SEQUENCE: 30
ctgtctactg gggtctcttt cttttcctg tcttttcaca tttcaaacct ccagtttaat      60
tcctctctgg aagatcccag caccgactac taccaagagc tgcagagaga catttctgaa   120 atgttttgc agattataa acaagggggt tttctgggcc tctccaatat taagttcagg     180
ccaggatctg tggtggtaca attgactctg gccttccgag aaggtaccat caatgtccac   240
gacatggaga cacagttcaa tcagtataaa acggaagcag cctctcgata taacctgacg   300
atctcagacg tcagcgtgag tgatgtgcca tttcct                              336

<210> SEQ ID NO 31
<211> LENGTH: 66
<212> TYPE: PRT
<213> ORGANISM: Homo sapiens

<400> SEQUENCE: 31

Ile Pro Ala Pro Thr Thr Thr Lys Ser Cys Arg Glu Thr Phe Leu Lys
1               5                   10                  15

Trp Pro Gly Ser Val Val Gln Leu Thr Leu Ala Phe Arg Glu Gly
            20                  25                  30

Thr Ile Asn Val His Asp Val Glu Thr Gln Phe Asn Gln Tyr Lys Thr
        35                  40                  45

Glu Ala Ala Ser Arg Tyr Asn Leu Thr Ile Ser Asp Val Ser Val Ser
    50                  55                  60

Asp Val
65

<210> SEQ ID NO 32
<211> LENGTH: 198
<212> TYPE: DNA
<213> ORGANISM: Homo sapiens

<400> SEQUENCE: 32
atcccagcac cgactactac caagagctgc agagagacat ttctgaaatg ccaggatct     60 gtggtggtac aattgactct ggccttccga gaaggtacca tcaatgtcca cgacatggag   120
acacagttca atcagtataa acggaagcag cctctcgat ataacctgac gatctcagac    180
gtcagcgtga gtgatgtg                                                  198

<210> SEQ ID NO 33
<211> LENGTH: 232
<212> TYPE: PRT
<213> ORGANISM: Homo Sapiens

<400> SEQUENCE: 33

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
```

```
                    100                 105                 110
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Val Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 34
<211> LENGTH: 699
<212> TYPE: DNA
<213> ORGANISM: Homo Sapiens

<400> SEQUENCE: 34
gagcccaaat cttgtgacaa aactcacaca tgcccaccgt gcccagcacc tgaactcctg      60
gggggaccgt cagtcttcct cttccccca aaacccaagg acaccctcat gatctcccgg     120
accccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgtcgg ctccttcttc ctctacagca agctcaccgt ggacaagagc     600
aggtggcagc aggggaacgt cttctcatgc tccgtgatgc atgaggctct gcacaaccac     660
tacacgcaga gagcctctc cctgtctccg ggtaaatga                            699

<210> SEQ ID NO 35
<211> LENGTH: 230
<212> TYPE: PRT
<213> ORGANISM: Homo Sapiens

<400> SEQUENCE: 35

Lys Ser Cys Asp Lys Pro His Thr Cys Pro Leu Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80
```

```
Ser Thr Tyr Arg Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Ala
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
210                 215                 220

Ser Leu Ser Pro Gly Lys
225                 230

<210> SEQ ID NO 36
<211> LENGTH: 690
<212> TYPE: DNA
<213> ORGANISM: Homo Sapiens

<400> SEQUENCE: 36
aaatcttgtg acaaacctca cacatgccca ctgtgcccag cacctgaact cctgggggga      60
ccgtcagtct tcctcttccc cccaaaaccc aaggacaccc tcatgatctc ccggacccct     120
gaggtcacat gcgtggtggt ggacgtgagc cacgaagacc ctgaggtcaa gttcaactgg     180
tacgtggacg gcgtggaggt gcataatgcc aagacaaagc cgcgggagga gcagtacaac     240
agcacgtacc gtgtggtcag cgtcctcacc gtcctgcacc aggactggct gaatggcaag     300
gagtacaagt gcaaggtctc caacaaagcc ctcccagccc ccatcgagaa aaccatctcc     360
aaagccaaag ggcagccccg agaaccacag gtgtacaccc tgcccccatc ccgggatgag     420
ctgaccaaga accaggtcag cctgacctgc ctagtcaaag gcttctatcc cagcgacatc     480
gccgtggagt gggagagcaa tgggcagccg gagaacaact acaaggccac gcctcccgtg     540
ctggactccg acggctcctt cttcctctac agcaagctca ccgtggacaa gagcaggtgg     600
cagcagggga acgtcttctc atgctccgtg atgcatgagg ctctgcacaa ccactacacg     660
cagaagagcc tctccctgtc tccgggtaaa                                     690

<210> SEQ ID NO 37
<211> LENGTH: 228
<212> TYPE: PRT
<213> ORGANISM: Homo Sapiens

<400> SEQUENCE: 37

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45
```

His Glu Asp Pro Glu Val Gln Phe Asn Trp Tyr Val Asp Gly Met Glu
         50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
    210                 215                 220

Ser Pro Gly Lys
225

<210> SEQ ID NO 38
<211> LENGTH: 687
<212> TYPE: DNA
<213> ORGANISM: Homo Sapiens

<400> SEQUENCE: 38
gagcgcaaat gttgtgtcga gtgcccaccg tgcccagcac cacctgtggc aggaccgtca        60
gtcttcctct tccccccaaa acccaaggac accctcatga tctcccggac ccctgaggtc       120
acgtgcgtgg tggtggacgt gagccacgaa gaccccgagg tccagttcaa ctggtacgtg       180
gacggcatgg aggtgcataa tgccaagaca aagccacggg aggagcagtt caacagcacg       240
ttccgtgtgg tcagcgtcct caccgtcgtg caccaggact ggctgaacgg caaggagtac       300
aagtgcaagg tctccaacaa aggcctccca gcccccatcg agaaaaccat ctccaaaacc       360
aaagggcagc cccgagaacc acaggtgtac accctgcccc catcccggga ggagatgacc       420
aagaaccagg tcagcctgac ctgcctggtc aaaggcttct accccagcga catcgccgtg       480
gagtgggaga gcaatgggca gccggagaac aactacaaga ccacacctcc catgctggac       540
tccgacggct ccttcttcct ctacagcaag ctcaccgtgg acaagagcag gtggcagcag       600
gggaacgtct tctcatgctc cgtgatgcat gaggctctgc acaaccacta cacacagaag       660
agcctctccc tgtctccggg taaatga                                          687

<210> SEQ ID NO 39
<211> LENGTH: 229
<212> TYPE: PRT
<213> ORGANISM: Homo Sapiens

<400> SEQUENCE: 39

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr

```
                20                  25                  30
Leu Met Ile Ser Arg Thr Pro Glu Val Thr Cys Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 40
<211> LENGTH: 690
<212> TYPE: DNA
<213> ORGANISM: Homo Sapiens

<400> SEQUENCE: 40
gagtccaaat atggtccccc atgcccatca tgcccagcac ctgagttcct gggggggacca      60 tcagtcttcc tgttcccccc aaaacccaag gacactctca tgatctcccg gacccctgag     120
gtcacgtgcg tggtggtgga cgtgagccag gaagacccccg aggtccagtt caactggtac     180
gtggatggcg tggaggtgca taatgccaag acaaagccgc gggaggagca gttcaacagc     240
acgtaccgtg tggtcagcgt cctcaccgtc ctgcaccagg actggctgar cggcaaggag     300
tacaagtgca aggtctccar caaaggcctc ccgtcctcca tcgagaaaac catctccaam     360 gccamgggc agccccgaga gccacaggtg tacaccctgc ccccatccca ggaggagatg     420
accaagaacc aggtcagcct gacctgcctg gtcaaaggct tctacccag cgacatcgcc     480 gtggagtggg agagcaatgg gcagccggag aacaactaca agaccacgcc tcccgtgctg     540
gactccgacg gctccttctt cctctacagc aggctaaccg tggacaagag cagktggcag     600
gaggggaatg tcttctcatg ctccgtgatg catgaggctc tgcacaacca ctacacacag     660
aagagcctct ccctgtctct gggtaaatga                                      690

<210> SEQ ID NO 41
<211> LENGTH: 585
<212> TYPE: PRT
<213> ORGANISM: Homo Sapiens

<400> SEQUENCE: 41
```

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Gln Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Pro Asp Pro His Glu
            355                 360                 365

Cys Tyr Ala Lys Val Phe Asp Glu Phe Lys Pro Leu Met Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
```

```
                    420              425              430
Val Gly Ser Lys Cys Cys Lys His Pro Glu Ala Lys Arg Met Pro Cys
            435                  440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 42
<211> LENGTH: 1758
<212> TYPE: DNA
<213> ORGANISM: Homo Sapiens

<400> SEQUENCE: 42
gatgcacaca agagtgaggt tgctcatcgg tttaaagatt tgggagaaga aaatttcaaa        60
gccttggtgt tgattgcctt tgctcagtat cttcagcagt gtccatttga agatcatgta       120
aaattagtga atgaagtaac tgaatttgca aaaacatgtg ttgctgatga gtcagctgaa       180
aattgtgaca aatcacttca tacccttttt ggagacaaat tatgcacagt tgcaactctt       240
cgtgaaacct atggtgaaat ggctgactgc tgtgcaaaac aagaacctga gaaaatgaa        300 tgcttcttgc aacacaaaga tgacaatcca atctccccc gattggtgag accagaggtt       360
gatgtgatgt gcactgcttt tcatgacaat gaagagacat ttttgaaaaa atacttatat       420
gaaattgcca agacatcc ttactttat gccccgcaac tccttttctt tgctaaaagg        480
tataaagctg cttttacaga atgttgccaa gctgctgata agcagcctg cctgttgcca       540 aagctcgatg aacttcggga tgaagggaag gcttcgtctg ccaaacagag actcaagtgt       600
gccagtctcc aaaaatttgg agaaagagct ttcaaagcat gggcagtagc tcgcctgagc       660
cagagatttc ccaaagctga gtttgcagaa gtttccaagt tagtgacaga tcttaccaaa       720
gtccacacgg aatgctgcca tggagatctg cttgaatgtg ctgatgacag gcggaccttt       780
gccaagtata tctgtgaaaa tcaagattcg atctccagta aactgaagga atgctgtgaa       840
aaacctctgt tggaaaaatc ccactgcatt gccgaagtgg aaaatgatga gatgcctgct       900
gacttgcctt cattagcggc tgattttgtt gaaagtaagg atgtttgcaa aaactatgct       960
gaggcaaagg atgtcttctt gggcatgttt ttgtatgaat atgcaagaag gcatcctgat      1020
tactctgtcg tactgctgct gagacttgcc aagacatatg aaaccactct agagaagtgc      1080
tgtgccgctc cagatcctca tgaatgctat gccaaagtgt tcgatgaatt taaacctctt      1140
atggaagagc ctcagaattt aatcaaacaa aattgtgagc tttttgagca gcttggagag      1200
```

```
tacaaattcc agaatgcgct attagttcgt tacaccaaga aagtacccca agtgtcaact    1260
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagcttgtga acacaagcc caaggcaaca    1620 aaagagcaac tgaaagctgt tatggatgat ttcgcagctt ttgtagagaa gtgctgcaag    1680
gctgacgata aggaaacctg cttttgccgag gagggtaaaa aacttgttgc tgcaagtcaa    1740
gctgccttag gcttataa                                                  1758

<210> SEQ ID NO 43
<211> LENGTH: 110
<212> TYPE: PRT
<213> ORGANISM: Homo Sapiens

<400> SEQUENCE: 43

Met Arg Phe Met Thr Leu Leu Phe Leu Thr Ala Leu Ala Gly Ala Leu
1               5                   10                  15

Val Cys Ala Tyr Asp Pro Glu Ala Ala Ser Ala Pro Gly Ser Gly Asn
            20                  25                  30

Pro Cys His Glu Ala Ser Ala Ala Gln Lys Glu Asn Ala Gly Glu Asp
        35                  40                  45

Pro Gly Leu Ala Arg Gln Ala Pro Lys Pro Arg Lys Gln Arg Ser Ser
    50                  55                  60

Leu Leu Glu Lys Gly Leu Asp Gly Ala Lys Lys Ala Val Gly Gly Leu
65                  70                  75                  80

Gly Lys Leu Gly Lys Asp Ala Val Glu Asp Leu Glu Ser Val Gly Lys
                85                  90                  95

Gly Ala Val His Asp Val Lys Asp Val Leu Asp Ser Val Leu
            100                 105                 110

<210> SEQ ID NO 44
<211> LENGTH: 333
<212> TYPE: DNA
<213> ORGANISM: Homo Sapiens

<400> SEQUENCE: 44
atgaggttca tgactctcct cttcctgaca gctctggcag gagccctggt ctgtgcctat     60
gatccagagg ccgcctctgc cccaggatcg gggaaccctt gccatgaagc atcagcagct    120
caaaaggaaa atgcaggtga agacccaggg ttagccagac aggcaccaaa gccaaggaag    180
cagagatcca gccttctgga aaaaggccta gacggagcaa aaaaagctgt gggggggactc    240 ggaaaactag gaaaagatgc agtcgaagat ctagaaagcg tgggtaaagg agccgtccat    300
gacgttaaag acgtccttga ctcagtacta tag                                 333

<210> SEQ ID NO 45
<211> LENGTH: 21
<212> TYPE: DNA
<213> ORGANISM: Artificial
<220> FEATURE:
<223> OTHER INFORMATION: Synthesized Sequence

<400> SEQUENCE: 45
aacccttgcc atgaagcatc a                                               21
```

<210> SEQ ID NO 46
<211> LENGTH: 21
<212> TYPE: DNA
<213> ORGANISM: Artificial
<220> FEATURE:
<223> OTHER INFORMATION: Synthesized Sequence

<400> SEQUENCE: 46
aagcatcagc agctcaaaag g                                            21

<210> SEQ ID NO 47
<211> LENGTH: 21
<212> TYPE: DNA
<213> ORGANISM: Artificial
<220> FEATURE:
<223> OTHER INFORMATION: Synthesized Sequence

<400> SEQUENCE: 47
aaaaggaaaa tgcaggtgaa g                                            21

<210> SEQ ID NO 48
<211> LENGTH: 21
<212> TYPE: DNA
<213> ORGANISM: Artificial
<220> FEATURE:
<223> OTHER INFORMATION: Synthesized Sequence

<400> SEQUENCE: 48
aaaggaaaat gcaggtgaag a                                            21

<210> SEQ ID NO 49
<211> LENGTH: 21
<212> TYPE: DNA
<213> ORGANISM: Artificial
<220> FEATURE:
<223> OTHER INFORMATION: Synthesized Sequence

<400> SEQUENCE: 49
aaggaaaatg caggtgaaga c                                            21

<210> SEQ ID NO 50
<211> LENGTH: 21
<212> TYPE: DNA
<213> ORGANISM: Artificial
<220> FEATURE:
<223> OTHER INFORMATION: Sythesized Sequence

<400> SEQUENCE: 50
aaaatgcagg tgaagaccca g                                            21

<210> SEQ ID NO 51
<211> LENGTH: 21
<212> TYPE: DNA
<213> ORGANISM: Artificial
<220> FEATURE:
<223> OTHER INFORMATION: Synthesized sequence

<400> SEQUENCE: 51
aaatgcaggt gaagacccag g                                            21

<210> SEQ ID NO 52
<211> LENGTH: 21
<212> TYPE: DNA
<213> ORGANISM: Artificial
<220> FEATURE:
<223> OTHER INFORMATION: Synthesized Sequence

<400> SEQUENCE: 52
aaagccaagg aagcagagat c                                              21

<210> SEQ ID NO 53
<211> LENGTH: 21
<212> TYPE: DNA
<213> ORGANISM: Artificial
<220> FEATURE:
<223> OTHER INFORMATION: Synthesized Sequence

<400> SEQUENCE: 53
aagccaagga agcagagatc c                                              21

<210> SEQ ID NO 54
<211> LENGTH: 21
<212> TYPE: DNA
<213> ORGANISM: Artificial
<220> FEATURE:
<223> OTHER INFORMATION: Synthesized Sequence

<400> SEQUENCE: 54
aaggaagcag agatccagcc t                                              21

<210> SEQ ID NO 55
<211> LENGTH: 21
<212> TYPE: DNA
<213> ORGANISM: Artificial
<220> FEATURE:
<223> OTHER INFORMATION: Synthesized Sequence

<400> SEQUENCE: 55
aagcagagat ccagccttct g                                              21

<210> SEQ ID NO 56
<211> LENGTH: 21
<212> TYPE: DNA
<213> ORGANISM: Artificial
<220> FEATURE:
<223> OTHER INFORMATION: Synthesized Sequence

<400> SEQUENCE: 56
aaaaaggcct agacggagca a                                              21

<210> SEQ ID NO 57
<211> LENGTH: 21
<212> TYPE: DNA
<213> ORGANISM: Artificial
<220> FEATURE:
<223> OTHER INFORMATION: Synthesized sequence

<400> SEQUENCE: 57
aaaaggccta gacggagcaa a                                              21

<210> SEQ ID NO 58
<211> LENGTH: 21
<212> TYPE: DNA
<213> ORGANISM: Artificial
<220> FEATURE:
<223> OTHER INFORMATION: Synthesized Sequence

<400> SEQUENCE: 58
aaaggcctag acggagcaaa a                                              21

<210> SEQ ID NO 59
<211> LENGTH: 21

```
<212> TYPE: DNA
<213> ORGANISM: Artificial
<220> FEATURE:
<223> OTHER INFORMATION: Synthesized Sequence

<400> SEQUENCE: 59
aaggcctaga cggagcaaaa a                                              21

<210> SEQ ID NO 60
<211> LENGTH: 21
<212> TYPE: DNA
<213> ORGANISM: Artificial
<220> FEATURE:
<223> OTHER INFORMATION: Synthesized Sequence

<400> SEQUENCE: 60
aaactaggaa aagatgcagt c                                              21

<210> SEQ ID NO 61
<211> LENGTH: 21
<212> TYPE: DNA
<213> ORGANISM: Artificial
<220> FEATURE:
<223> OTHER INFORMATION: Synthesized Sequence

<400> SEQUENCE: 61
aactaggaaa agatgcagtc g                                              21

<210> SEQ ID NO 62
<211> LENGTH: 21
<212> TYPE: DNA
<213> ORGANISM: Artificial
<220> FEATURE:
<223> OTHER INFORMATION: Synthesized Sequence

<400> SEQUENCE: 62
aaaagatgca gtcgaagatc t                                              21

<210> SEQ ID NO 63
<211> LENGTH: 21
<212> TYPE: DNA
<213> ORGANISM: Artificial
<220> FEATURE:
<223> OTHER INFORMATION: Synthesized Sequence

<400> SEQUENCE: 63
aaagatgcag tcgaagatct a                                              21

<210> SEQ ID NO 64
<211> LENGTH: 21
<212> TYPE: DNA
<213> ORGANISM: Artificial
<220> FEATURE:
<223> OTHER INFORMATION: Synthesized Sequence

<400> SEQUENCE: 64
aagatgcagt cgaagatcta g                                              21

<210> SEQ ID NO 65
<211> LENGTH: 21
<212> TYPE: DNA
<213> ORGANISM: Artificial
<220> FEATURE:
<223> OTHER INFORMATION: Synthesized Sequence

<400> SEQUENCE: 65
aagatctaga aagcgtgggt a                                              21
```

<210> SEQ ID NO 66
<211> LENGTH: 21
<212> TYPE: DNA
<213> ORGANISM: Artificial
<220> FEATURE:
<223> OTHER INFORMATION: Synthesized Sequence

<400> SEQUENCE: 66
aaaggagccg tccatgacgt t					21

<210> SEQ ID NO 67
<211> LENGTH: 21
<212> TYPE: DNA
<213> ORGANISM: Artificial
<220> FEATURE:
<223> OTHER INFORMATION: Synthesized Sequence

<400> SEQUENCE: 67
aaggagccgt ccatgacgtt a					21

<210> SEQ ID NO 68
<211> LENGTH: 21
<212> TYPE: DNA
<213> ORGANISM: Artificial
<220> FEATURE:
<223> OTHER INFORMATION: Synthesized Sequence

<400> SEQUENCE: 68
aaagacgtcc ttgactcagt a					21

<210> SEQ ID NO 69
<211> LENGTH: 21
<212> TYPE: DNA
<213> ORGANISM: Artificial
<220> FEATURE:
<223> OTHER INFORMATION: Synthesized Sequence

<400> SEQUENCE: 69
aagacgtcct tgactcagta c					21

<210> SEQ ID NO 70
<211> LENGTH: 334
<212> TYPE: PRT
<213> ORGANISM: Artificial
<220> FEATURE:
<223> OTHER INFORMATION: Recombinant Sequence

<400> SEQUENCE: 70

```
Phe Asn Ser Ser Leu Glu Asp Pro Ser Thr Asp Tyr Tyr Gln Glu Leu
 1               5                  10                  15

Gln Arg Asp Ile Ser Glu Met Phe Leu Gln Ile Tyr Lys Gln Gly Gly
                20                  25                  30

Phe Leu Gly Leu Ser Asn Ile Lys Phe Arg Pro Gly Ser Val Val Val
            35                  40                  45

Gln Leu Thr Leu Ala Phe Arg Glu Gly Thr Ile Asn Val His Asp Val
        50                  55                  60

Glu Thr Gln Phe Asn Gln Tyr Lys Thr Glu Ala Ala Ser Arg Tyr Asn
 65                  70                  75                  80

Leu Thr Ile Ser Asp Val Ser Val Ser Asp Val Pro Phe Pro Phe Ser
                85                  90                  95

Ala Gln Ser Gly Ala Gly Lys Leu Lys Ser Cys Asp Lys Pro His Thr
            100                 105                 110
```

```
        Cys Pro Leu Cys Pro Ala Pro Glu Leu Leu Gly Gly Pro Ser Val Phe
                    115                 120                 125

Leu Phe Pro Pro Lys Pro Lys Asp Thr Leu Met Ile Ser Arg Thr Pro
            130                 135                 140

Glu Val Thr Cys Val Val Val Asp Val Ser His Glu Asp Pro Glu Val
        145                 150                 155                 160

Lys Phe Asn Trp Tyr Val Asp Gly Val Glu Val His Asn Ala Lys Thr
                        165                 170                 175

Lys Pro Arg Glu Glu Gln Tyr Asn Ser Thr Tyr Arg Val Val Ser Val
                    180                 185                 190

Leu Thr Val Leu His Gln Asp Trp Leu Asn Gly Lys Glu Tyr Lys Cys
            195                 200                 205

Lys Val Ser Asn Lys Ala Leu Pro Ala Pro Ile Glu Lys Thr Ile Ser
        210                 215                 220

Lys Ala Lys Gly Gln Pro Arg Glu Pro Gln Val Tyr Thr Leu Pro Pro
        225                 230                 235                 240

Ser Arg Asp Glu Leu Thr Lys Asn Gln Val Ser Leu Thr Cys Leu Val
                        245                 250                 255

Lys Gly Phe Tyr Pro Ser Asp Ile Ala Val Glu Trp Glu Ser Asn Gly
                    260                 265                 270

Gln Pro Glu Asn Asn Tyr Lys Ala Thr Pro Pro Val Leu Asp Ser Asp
            275                 280                 285

Gly Ser Phe Phe Leu Tyr Ser Lys Leu Thr Val Asp Lys Ser Arg Trp
        290                 295                 300

Gln Gln Gly Asn Val Phe Ser Cys Ser Val Met His Glu Ala Leu His
        305                 310                 315                 320

Asn His Tyr Thr Gln Lys Ser Leu Ser Leu Ser Pro Gly Lys
                        325                 330

<210> SEQ ID NO 71
<211> LENGTH: 1002
<212> TYPE: DNA
<213> ORGANISM: Artificial
<220> FEATURE:
<223> OTHER INFORMATION: Recombinant Sequence

<400> SEQUENCE: 71
tttaattcct ctctggaaga tcccagcacc gactactacc aagagctgca gagagacatt      60
tctgaaatgt ttttgcagat ttataaacaa gggggttttc tgggcctctc caatattaag     120
ttcaggccag atctgtggt ggtacaattg actctggcct tccgagaagg taccatcaat      180
gtccacgaca tggagacaca gttcaatcag tataaaacgg aagcagcctc tcgatataac     240
ctgacgatct cagacgtcag cgtgagtgat gtgccatttc cttctctgc ccagtctggg      300 gctgggaagc ttaaatcttg tgacaaacct cacacatgcc cactgtgccc agcacctgaa     360
ctcctggggg gaccgtcagt cttcctcttc cccccaaaac ccaaggacac cctcatgatc     420
tcccggaccc ctgaggtcac atgcgtggtg gtggacgtga gccacgaaga ccctgaggtc     480
aagttcaact ggtacgtgga cggcgtggag gtgcataatg ccaagacaaa gccgcgggag     540
gagcagtaca acagcacgta ccgtgtggtc agcgtcctca ccgtcctgca ccaggactgg     600
ctgaatggca aggagtacaa gtgcaaggtc tccaacaaag ccctcccagc ccccatcgag     660
aaaaccatct ccaaagccaa agggcagccc cgagaaccac aggtgtacac cctgccccca     720
tcccgggatg agctgaccaa gaaccaggtc agcctgacct gcctagtcaa aggcttctat     780
cccagcgaca tcgccgtgga gtgggagagc aatgggcagc cggagaacaa ctacaaggcc     840
```

-continued

```
acgcctcccg tgctggactc cgacggctcc ttcttcctct acagcaagct caccgtggac    900
aagagcaggt ggcagcaggg gaacgtcttc tcatgctccg tgatgcatga ggctctgcac    960
aaccactaca cgcagaagag cctctccctg tctccgggta aa                     1002
```

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide

<400> SEQUENCE: 72

```
Phe Arg Pro Gly Ser Val Val Val
1               5
```

US 8,129,506 B2

MODULATION OF THE INTERACTION OF MUC1 WITH MUC1 LIGANDS

This application is a national phase application under 35 U.S.C. §371 of the International Application No. PCT/US2004/034,680 filed Oct. 21, 2004, which claims priority to U.S. Provisional application Ser. No. 60/514,198, filed Oct. 24, 2003, U.S. Provisional application Ser. No. 60/519,822, filed Nov. 12, 2003, and International Application No. PCT/US2004/034680, filed Oct. 21, 2004. The entire contents of each of the above-referenced disclosures is incorporated herein by reference.

FIELD OF THE INVENTION

The present invention relates generally to the field of cancer therapy, and more specifically, to the use of modulators or agents that interact with MUC1 as a point on intervention in cancer therapy.

BACKGROUND OF THE INVENTION

The human DF3/MUC1 transmembrane glycoprotein is aberrantly overexpressed by breast and other types of carcinomas (Kufe et al., 1984). MUC1 expression is localized to the apical borders of normal secretory epithelial cells. In carcinoma cells, loss of polarity is associated with expression of MUC1 at high levels over the entire cell surface (Kufe et al., 1984). Significantly, overexpression of MUC1 blocks apoptosis and is sufficient to confer cellular transformation (Li et al., 2003b). The fall-length MUC1 protein (MUC1-REP) is cleaved into N- and C-terminal subunits (N-ter (or ectodomain, "ED") and C-ter) that reside as a heterodimer at the cell membrane (Ligtenberg et al., 1992; Parry et al., 2001). The >250 kDa N-terminal ectodomain contains variable numbers of conserved 20 amino acid tandem repeats (VNTR region) that are extensively modified by O-glycosylation (Gendler et al., 1988; Siddiqui et al., 1988). The ~25 kDa C-ter includes an extracellular region of 58 amino acids (or extracellular domain, "ECD"), a 28 amino acid transmembrane domain and a 72 amino acid cytoplasmic tail. β-catenin, a component of the adherens junction of mammalian epithelial cells, binds directly to a SAGNGGSSL motif in the MUC1 cytoplasmic domain (Yamamoto et al., 1997). The SAGNGGSSL motif also functions as a binding site for γ-catenin (plakoglobin) (Yamamoto et al., 1997). The MUC1 C-ter is expressed at the cell membrane and in the nucleus where it colocalizes with β-catenin (Li et al., 2003b; Li et al, 2003c) and γ-catenin (Li et al., 2003b).

The available evidence indicates that MUC1 functions in integrating signals from the Wnt and ErbB pathways. Glycogen synthase kinase 3β (GSK3β), an effector of Wnt signaling, phosphorylates MUC1 on serine in a SPY site adjacent to that for β/γ-catenin binding (Li et al., 1998). GSK3β-mediated phosphorylation of MUC1 decreases the interaction between MUC1 and β-catenin (Li et al., 1998). The tyrosine in the SPY site is phosphorylated by c-Src and, in contrast to the effects of GSK3β, c-Src increases the interaction between MUC1 and β-catenin (Li et al., 2001a). Phosphorylation of the MUC1 tail by protein kinase Cδ (PKCδ) also contributes to the interactions between MUC1 and β-catenin Ren et al., 2002). Other studies have shown that MUC1 forms a complex with the epidermal growth factor receptor (EGFR) (Li et al., 2001b; Schroeder et al., 2001). Stimulation of cells with EGF is associated with tyrosine phosphorylation of the SPY site and increased formation of MUC1-β-catenin complexes (Li et al., 2001b). Conversely, exposure of cells to heregulin (HRG), a ligand for ErbB receptors, induces binding of MUC1 and γ-catenin (Li et al., 2003c).

A number of splice variants of MUC1 have been described, including transmembrane proteins that lack the entire VNTR region. Such isoforms include MUC1/Y, MUC1/X and MUC1/Z (Zrihan-Licht et al., 1994; Baruch et al., 1997; Oosterkamp et al., 1997; Obermair et al., 2002).

SUMMARY OF THE INVENTION

The present invention provides for chimeric proteins comprising a MUC1-extracellular (MUC1-EC) polypeptide and a carrier polypeptide that function as traps for endogenous MUC1 ligands. For the purposes of the present invention, "MUC1-EC polypeptide" means a polypeptide derived from MUC1 REP extracellular domain or ectodomain or the extracellular domains of MUC1 transmembrane isoforms such as MUC1/Y, MUC1/X and MUC1/Z. "Carrier polypeptide" means a polypeptide that, when present in a chimeric protein comprising a MUC1-EC polypeptide, will increase the serum half-life of the chimeric protein as compared to the serum half-life of the MUC1-EC polypeptide alone. Examples of carrier polypeptides include those derived from human immunoglobulin FC polypeptides and those derived from human albumin polypeptides. A "MUC1 ligand trap" means a polypeptide that will bind to a MUC1 ligand. "MUC1 ligand" means a ligand that binds to the extracellular and/or ectodomain, excluding the VNTR region, of MUC1 or binds to the extracellular domain of MUC1 isoforms that lack the VNTR region. By "trapping" MUC1 ligands, the MUC1-EC chimeric proteins of the present invention intercept MUC1 ligands prior to binding to MUC1 presented on the plasma membrane of cancer cells and thereby decrease or substantially prevent MUC1-mediated oncogenic signaling.

One aspect of the present invention is a MUC1 chimeric protein, which may be a fusion protein, comprising a first polypeptide sequence and a second polypeptide sequence, wherein the first polypeptide sequence is a MUC1-EC polypeptide and the second polypeptide sequence is a carrier polypeptide which may be a human immunoglobulin FC polypeptide or a human albumin polypeptide. In various embodiments, the MUC1-EC polypeptide is selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 and SEQ ID NO: 31. In some embodiments, the MUC1-EC polypeptide binds dermcidin and/or PLU-1. In some embodiments the human immunoglobulin FC polypeptide is a human IgG FC polypeptide, which may be a IgG1 or IgG2 FC polypeptide. In some embodiments, a MUC1 chimeric protein comprising an immunoglobulin FC polypeptide may further comprise a second MUC1 chimeric protein comprising an immunoglobulin FC polypeptide, wherein the two MUC1 chimeric proteins comprising immunoglobulin FC polypeptides form a dimer by means of one or more disulfide bridges formed between the hinge regions of the immunoglobulin FC polypeptides. The two MUC1-EC polypeptides in the dimer may be the same or different.

The invention also encompasses a pharmaceutical composition comprising a pharmaceutically acceptable carrier and a MUC1 chimeric protein comprising a first polypeptide sequence and a second polypeptide sequence, wherein the first polypeptide sequence is a MUC1-polypeptide and the second polypeptide sequence is a carrier polypeptide.

Other aspects of the invention include methods of inhibiting or killing a MUC1-expressing cancer cell comprising contacting the MUC1-expressing cancer cell with an effective amount of a MUC1 chimeric protein comprising a first polypeptide sequence and a second polypeptide sequence, wherein the first polypeptide sequence is a MUC1-EC polypeptide and the second polypeptide sequence is a carrier polypeptide, which may be a human immunoglobulin FC polypeptide or a human albumin polypeptide. A MUC1-expressing cancer cell means a cancer cell that expresses MUC1-REP and/or one or more types of transmembrane MUC1 isoforms lacking the VNTR region. The methods may further comprise contacting the MUC1-expressing cancer cell with an effective amount of a chemotherapeutic agent or exposing the MUC1-expressing cancer cell with an effective dose of ionizing radiation.

A further aspect of the present invention is a method of treating cancer in a patient comprising administering an effective amount of MUC1 chimeric protein comprising a first polypeptide sequence and a second polypeptide sequence, wherein the first polypeptide sequence is a MUC1-EC polypeptide and the second polypeptide sequence is a carrier polypeptide, which may be a human immunoglobulin FC polypeptide or a human albumin polypeptide.

Another aspect of the present invention provides for the modulation of the binding of dermcidin to MUC1 in addition to the use of the MUC1 ligand trap described above. Thus, the present invention provides for methods of inhibiting the expression of dermcidin through gene silencing, inhibition of dermcidin-dependent signaling via use of dermcidin antibodies and aptamers. The invention also provides for screening methods for the identification of compounds that inhibit the binding of dermcidin to MUC1.

DETAILED DESCRIPTION OF THE INVENTION

I. Polypeptides

The present invention provides for chimeric proteins comprising a MUC1-EC polypeptide and a carrier polypeptide. Such chimeric proteins may be provided as fusion proteins or proteins wherein the MUC1-EC polypeptide and carrier polypeptide are otherwise chemically linked together.

The polypeptides of the present invention include variant polypeptides. By "variant" polypeptide is intended a polypeptide sequence modified by deletion or addition of one or more amino acids at one or more sites in the sequence; or substitution of one or more amino acids at one or more sites within the sequence. Variant polypeptides encompassed by the present invention retain the desired biological activity of the polypeptide from which they are derived. Such variants will have at least 40%, 50%, 60%, 70%, generally at least 75%, 80%, 85%, preferably about 90% to 95% or more, and more preferably about 98% or more sequence identity to the amino acid sequence of the polypeptide from which they are derived. The percentage of sequence identity, also termed homology, between a polypeptide native and a variant sequence may be determined by comparing the two sequences using the Gap program (Wisconsin Sequence Analysis Package, Version 8 for Unix, Genetics Computer Group, University Research Park, Madison Wis.), which uses the algorithm of Smith and Waterman, (1981).

The polypeptides of the present invention also include variant polypeptides with one or more conservative substitutions. For the purposes of classifying amino acid substitutions as conservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class.

Also encompassed by the present invention are chemical derivatives of polypeptides. "Chemical derivative" refers to a subject polypeptide having one or more residues chemically derivatized by reaction of a functional side group. Such derivatized residues include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hyrazides. Free hydroxyl groups may be derivatized to form O-acyl or O-alkyl derivatives. The imadazole group of histidine may be derivatized to form N-imbenzylhistidine.

The term "polypeptide" as used herein indicates a molecular chain of amino acids and does not refer to a specific length of the product.

A. MUC1-ECD Polypeptides

The present invention relates to chimeric proteins comprising MUC1-EC polypeptides. MUC1-EC polypeptides may be derived from the sequence for MUC1-REP, wherein tandem repeats may be present, as in SEQ ID NO:13, or all tandem repeat sequences are deleted, as in SEQ ID NO:15. Further deletions may be made from the amino-terminal, such as exemplified in SEQ ID NO:17, 19, and 23, or the carboxy-terminal, as exemplified in SEQ ID NO: 21. MUC1-REP is cleaved during intercellular processing between the glycine and the serine in the sequence FRPGSVVV (SEQ ID NO:72), wherein the amino-terminal and carboxy-terminal fragments associate as a heterodimer (Parry et al., 2001). The heterodimer is apparently very stable, being resistant to boiling, urea, sulfhydryl compounds, low pH or high salt (Julian & Carson, 2002), and thus would be expected to be purified as a heterodimer. Thus, the present invention also encompasses the heterodimer forms of MUC1-EC fusion proteins to the extent they are cleaved as in the intercellular processing of MUC1-REP.

MUC1 polypeptides may also be derived from the sequence for the splice variant MUC1/Y (see e.g., Zirhan-Licht et al., 1994; GenBank S48146[gi:1085342]), wherein SEQ ID NO: 1 and SEQ ID NO: 3 exemplify two amino-terminal variants. SEQ ID NO 11 represents a further 102 amino acid truncated from. The polynucleotide sequences for the forgoing MUC1-EC polypeptides are exemplified in SEQ ID NO: 2, 4, 6, 8, 10, 12, 14, 16 and 18.

MUC1-EC polypeptides are also derived from other MUC1 splice variants. SEQ ID NO: 5 represents a MUC1-EC derived from a splice variant that has been called both MUC1/Z (Oosterkamp et al., 1997; GenBank AAD10858[gi: 4204967]) and MUC1/X (Baruch et al., 1997). SEQ ID NO: 7 represents a MUC1-EC derived from a splice variant that has been termed MUC1/V (WO9603502). SEQ ID NO: 9 represents a MUC1-EC derived from a splice variant that has been termed called MUC1/X (GenBank AAD10856[gi: 4204963]. The present invention also includes variants of SEQ ID NO: 5, 7 and 9 that comprise the longer amino-terminal sequence as found in SEQ ID NO: 1 and variants truncated from the amino-terminus, e.g., SEQ ID NO: 25 and 27, and/or from the carboxy-terminus, e.g., SEQ ID NO: 29 and 31.

The polynucleotide sequences for the foregoing exemplified MUC1-EC polypeptides are provided in SEQ ID NO: 2, 4, 6, 8, 10, 12, 14, 16, 18, 20, 22, 24, 26, 28, 30 and 32.

In one aspect of the present invention, the MUC1-EC polypeptide is SEQ ID NO: 1, SEQ ID NO: 3, SEQ ID NO: 7, or a fragment or substitutional variant thereof that binds dermcidin (DCD), Y-P30 peptide, and/or PLU-1. DCD is a diffusible neural survival evasion peptide (Cunningham et al. 2002) that has been proposed as a candidate oncogene in breast cancer (Porter et al., 2003). Y-P30 is a DCD derived peptide that retains the neuronal survival promoting properties (Cunningham, 1998; Cunningham 2000). PLU-1 is a nuclear protein that is up-regulated in breast cancer (Barret et al., 2002).

B. Immunoglobulin Polypeptides

One aspect of the present invention encompasses MUC1-EC chimeric proteins comprising the FC portion of human immunoglobulins as a carrier polypeptide. The basic unit of an immunoglobulin molecule consists of two identical heavy chains and two identical light chains. The amino-terminus of each chain contains a region of variable amino acid sequence (variable region). The variable regions of the heavy and light chains interact to form two antigen binding sites. The carboxy-terminus of each chain contains a region of constant amino acid sequence (constant region). The light chain contains a single constant domain, whereas the heavy chain constant domain is subdivided into four rate domains (CH1, hinge, CH2, and CH3). The heavy chains of immunoglobulin molecules are of several types, including mu (M), delta (D), gamma (G), alpha (A) and epsilon (E). An immunoglobulin molecule derives its name from the type of heavy chain that it possesses.

"FC" originally stood for "fragment crystallizable" and is derived from a rabbit IgG antibody fragment isolated and defined following digestion with papain. "FC" is now more usefully thought as "fragment complement binding" and generally comprises the C-terminal half of the heavy chain including that part of the hinge region containing the heavy-chain disulphide bridges. The FC portion of immunoglobulins controls the rate of catabolism of the molecules (serum half-lives in the range of two to three weeks). For the purposes of the present invention, "FC" means an immunoglobulin fragment comprising the CH2 and CH3 domains and wherein the hinge region is present, partially present, modified by deletions or substitutions, or is absent. "Human FC" means an FC portion derived from heavy chain types G, M, D, A and E.

SEQ ID NO: 33 represents the amino acid sequence of the hinge, CH2 and CH3 regions of IgG1, and is capable of forming dimers via inter-chain disulfide bridges via the cysteines at residues 11 and 14. SEQ ID NO: 34 provides the corresponding coding polynucleotide sequence for SEQ ID NO: 33. Embodiments of the present invention include the full sequence of SEQ ID NO: 33 and truncated versions, such as deletion of the first five amino acids, the cysteine at residues 5, or the full hinge region (first amino-terminal 16 amino acid residues). Other embodiments encompass suitable mutations, such as substitution of alanine for the cysteine at residue position 5. An example of a variant IgG1 polypeptide sequence is shown in SEQ ID NO: 35, coded by the polynucleotide sequence shown in SEQ ID NO: 36.

SEQ ID NO: 37 represents the amino acid sequence of the hinge, CH2 and CH3 regions of IgG2. SEQ ID NO: 38 provides the corresponding coding polynucleotide sequence for SEQ ID NO: 37. Embodiments of the invention include in addition to the full sequence of SEQ ID NO: 37, deletions and substitutional deletions of the hinge region, i.e., amino-terminal 12 amino acid residues, including deletion of all the hinge region or deletion or substitution of one or more of the cysteine residues.

SEQ ID NO: 39 represents the amino acid sequence of the hinge, CH2 and CH3 regions of IgG4. SEQ ID NO: 40 provides the corresponding coding polynucleotide sequence for SEQ ID NO: 39. Embodiments of the invention include in addition to the full sequence of SEQ ID NO: 39, deletions and substitutional deletions of the hinge region, i.e., amino-terminal 12 amino acid residues, including deletion of all the hinge region or deletion or substitution of one or more of the cysteine residues. In one example of a suitable substitution, the serine at amino acid residue 10 is substituted with proline. Also, substitutions may be made in the CH2 region, for example, the leucine at amino acid residue 17 is substituted with glutamate.

MUC1-EC chimeric proteins comprising immunoglobulin FC polypeptides containing functional hinge regions are capable of forming dimers via disulfide bridges. Such dimers are encompassed by the present invention wherein the dimers may comprise the same or different MUC1-EC polypeptides.

C. Albumin Polypeptides

One aspect of the present invention encompasses MUC1-ECD fusion proteins comprising a carrier polypeptide derived from albumin. Human albumin is an abundant non-glycosylated plasma protein with a slow clearance profile and has been employed as a fusion partner to slow the clearance of other proteins (see e.g., Yeh et al., 1992, incorporated herein by reference). The terms, human serum albumin (HSA) and human albumin (HA) are used interchangeably herein. The amino acid and polynucleotide sequences for albumin are provided in SEQ ID NO: 41 and 42 respectively. The fusion proteins of the invention encompass MUC1-EC chimeric proteins comprising the full sequence of SEQ ID NO: 41 plus truncated albumins and/or albumins modified by substitutions, e.g., as described in U.S. Pat. Nos. 5,965,386, 5,380, 712 and 5,766,883, all incorporated herein by reference.

II. Chimeric Proteins

The present invention provides for chimeric proteins comprising a MUC1-EC polypeptide and a carrier polypeptide. Such chimeric proteins may be MUC1-EC fusion proteins and isolated DNA sequences encoding the MUC1-EC fusion proteins are also provided by the present invention. A DNA sequence encoding a fusion protein of the present invention is constructed using recombinant DNA techniques to insert DNA fragments encoding the MUC1-EC or carrier polypeptides into an appropriate expression vector. The 3' end of a DNA fragment encoding a MUC1-ECD is ligated (via a peptide linker) to the 5' end of the DNA fragment encoding a carrier polypeptide with the reading frames of the sequences in phase to permit translation of the mRNA into a single fusion protein. Alternatively, the 3' end of a DNA fragment encoding a carrier protein may be ligated (via a peptide linker) to the 5' end of the DNA fragment encoding a MUC1-EC, with the reading frames of the sequences in phase to permit translation of the mRNA into a single biologically active fusion protein. The MUC1-EC encoding sequence is preferably positioned upstream of the carrier polypeptide encoding sequence. A DNA sequence encoding an N-terminal signal sequence may be retained on the DNA sequence encoding the N-terminal polypeptide, while stop codons, which would prevent read-through to the downstream DNA sequence(s), are eliminated. Conversely, a stop codon required to end translation is generally retained on the DNA sequence encoding the C-terminal polypeptide. DNA encoding a signal sequence is preferably removed from DNA sequences other than those encoding the N-terminal polypeptide.

A DNA sequence encoding a desired peptide linker may be inserted between, and in the same reading frame as, the DNA sequences encoding MUC1-EC or carrier polypeptides using any suitable conventional technique. For example, a chemically synthesized oligonucleotide encoding the linker and containing appropriate restriction endonuclease cleavage sites may be ligated between the sequences encoding MUC1-EC or carrier polypeptide. Alternatively, a chemically synthesized DNA sequence may contain a sequence complementary to the 3' terminus (without the stop codon) of either MUC1-EC or carrier polypeptide followed by a linker-encoding sequence which is followed by a sequence complementary to the 5' terminus of the other of MUC1-EC or carrier polypeptide. Oligonucleotide directed mutagenesis is then employed to insert the linker-encoding sequence into a vector containing a direct fusion of MUC1-EC and carrier polypeptide. Another technique employs polymerase chain reactions using primers comprising, in part, single strand segments encoding a peptide linker. PCR-generated DNA fragments encoding two different proteins can be joined through annealing of the complementary single stranded linker-encoding segments present at a terminus of each fragment.

DNA sequences encoding MUC1-EC and carrier polypeptide may be isolated by any suitable conventional procedure, for use in constructing the fusion protein-encoding DNA sequences of the present invention. DNA sequences encoding fusion proteins to be expressed in a microorganism will typically contain no introns that could prematurely terminate transcription of DNA into mRNA; however, premature termination of transcription may be desirable, for example, where it would result in mutants having advantageous C-terminal truncations.

The coding sequence of MUC1-EC polypeptides may be obtained by isolating a sequence encoding a MUC1-EC from a recombinant cDNA or genomic DNA library. A cDNA library is preferably constructed by obtaining polyadenylated mRNA from a particular cell line which expresses a human MUC1-EC and using the mRNA as a template for synthesizing double-stranded cDNA. The double-stranded cDNA is then packaged into a recombinant vector, which is introduced into a host cell and propagated. MUC1-EC sequences contained in the cDNA library can be identified by screening the library with an appropriate nucleic acid probe which is capable of hybridizing with human MUC1-EC cDNA. Another cloning technique that may be employed is a direct expression procedure or DNAs encoding MUC1-EC polypeptides can be assembled by ligation of synthetic oligonucleotide subunits corresponding to all or part of the desired sequence.

DNA encoding soluble MUC1-EC and carrier polypeptides may be prepared by any of a number of conventional techniques. A DNA fragment encoding a desired soluble polypeptide may be subcloned into an expression vector. DNA fragments may be produced by restriction endonuclease digestion of a full-length cloned DNA sequence, and isolated by electrophoresis on agarose gels. Alternatively, a desired DNA sequence may be chemically synthesized using known techniques. Linkers containing restriction endonuclease cleavage site(s) may be employed to insert the desired DNA fragment into an expression vector, or the fragment may be digested at cleavage sites naturally present therein. The polymerase chain reaction (PCR) procedures also may be employed to isolate a DNA sequence encoding a desired soluble protein fragment.

In another approach, enzymatic treatment (using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The present invention provides recombinant expression vectors to express DNA encoding the fusion proteins of the present invention. The recombinant expression vectors are replicable DNA constructs which contain a synthetic or cDNA-derived DNA sequence encoding one of the above-described fusion proteins, operably linked to suitable transcriptional or translational regulatory elements. Examples of genetic elements having a regulatory role in gene expression include transcriptional promoters, operators or enhancers, a sequence encoding suitable mRNA ribosomal binding sites, and appropriate transcription and translation initiation and termination sequences. The ability to replicate in a host, usually conferred by an origin of replication, and a selection gene to facilitate recognition of transformants may additionally be incorporated. The regulatory elements employed in the expression vectors are generally derived from mammalian, microbial, viral, or insect genes. Expression vectors derived from retroviruses also may be employed.

DNA regions are operably linked when they are functionally related to each other. A DNA sequence encoding a fusion protein is said to be operably linked to one or more of the above-described regulatory elements when the fusion protein DNA sequence is transcribed, or the resulting mRNA is translated, under the control of the regulatory element(s).

Transformed host cells are cells that have been transformed or transfected with foreign DNA using recombinant DNA techniques. In the context of the present invention, the foreign DNA includes a sequence encoding the inventive fusion protein. Host cells may be transformed for purposes of cloning or amplifying the foreign DNA, or may be transformed with an expression vector for production of the fusion protein under the control of appropriate promoters. Suitable host cells include prokaryotes, yeast, or in some preferred embodiments, higher eukaryotic cell. Appropriate cloning and expression vectors for use with bacterial, fungal, yeast, and mammalian cellular hosts are described by Pouwels et al. (1985), the relevant disclosures of which is hereby incorporated by reference. Cell-free translation systems could also be employed to produce fusion protein using RNAs derived from the DNA constructs of the present invention.

Prokaryotes include gram negative or gram positive organisms. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Examples of suitable prokaryotic hosts for transformation include *E. coli*, bacilli such as *Bacillus subtilis, Salmonella typhimurium*, and various species within the genera *Pseudomonas, Streptomyces*, and *Staphylococcus*, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Amersham Biosciences, Piscataway, N.J.) and pGEM1 (Promega Biotec, Madison, Wis., USA). These pBR322 "backbone" sections are combined with an appropriate promoter and the structural sequence to be expressed.

E. coli is typically transformed using derivatives of pBR322, a plasmid derived from an E. coli species (Bolivar et al., 1977). pBR322 contains genes for ampicillin and tetracycline resistance, providing simple means for identifying transformed cells.

Promoters commonly used in recombinant microbial expression vectors include the b-lactamase (peniciluinase) and lactose promoter system (Chang et al., 1978; and Goeddel et al., 1979), the tryptophan (trp) promoter system (Goeddel et al., 1980) and tac promoter (Maniatis, 1982). A particularly useful bacterial expression system employs the phage $\lambda P_L$ promoter and cI857ts thermoinducible repressor. Plasmid vectors available from the American Type Culture Collection which incorporate derivatives of the $\lambda P_L$ promoter include plasmid pHUB2, resident in E. coli strain JMB9 (ATCC 37092) and pPLc28, resident in E. coli RR1 (ATCC 53082).

The recombinant fusion protein may also be expressed in yeast hosts, preferably from Saccharomyces species, such as S. cerevisiae. Yeast of other genera such as Pichia or Kluyveromyces may also be employed. Yeast vectors will generally contain an origin of replication from the 2 μm yeast plasmid or an autonomously replicating sequence (ARS), a promoter, DNA encoding the fusion protein, sequences for polyadenylation and transcription termination and a selection gene. Preferably, yeast vectors will include an origin of replication and selectable markers permitting transformation of both yeast and E. coli, e.g., the ampicillin resistance gene of E. coli and the S. cerevisiae trp 1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase.

Preferred yeast vectors can be assembled using DNA sequences from pBR322 for selection and replication in E. coli (Amp$^r$ gene and origin of replication) and yeast DNA sequences including a glucose-repressible ADH2 promoter and α-factor secretion leader. The ADH2 promoter has been described by Russell et al. (1982) and Beier et al., (1982). Advantageously, a DNA segment encoding a leader sequence functional in yeast is operably linked to the 5' end of the DNA encoding the fusion protein. The encoded leader peptide promotes secretion of the fusion protein from the host cell and is generally cleaved from the fusion protein upon secretion. As one example, the yeast α-factor leader, which directs secretion of heterologous proteins, can be inserted between the promoter and the structural gene to be expressed. See, e.g., Kurjan et al., (1982); Bitter et al., (1984). The leader sequence may be modified to contain, near its 3' end, one or more useful restriction sites to facilitate fusion of the leader sequence to foreign genes.

Suitable yeast transformation protocols are known to those of skill in the art. An exemplary technique is described by Hinnen et al. (1978), selecting for Trp$^+$ transformants in a selective medium consisting of 0.67% yeast nitrogen base, 0.5% casamino acids, 2% glucose, 10 μg/ml adenine and 20 μg/ml uracil. Host strains transformed by vectors comprising the above-described ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow & Summers, (1988). Established cell lines of mammalian origin may be employed. Examples of suitable mammalian host cell lines include the COS-7 lines of monkey kidney cells (described by Gluzman, 1981), L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment that also contains the SV40 viral origin or replication (Fiers et al., 1978). Smaller or larger SV40 fragments may also be used, provided the approximately 250 bp sequence extending from the Hind III site toward the BglI site located in the viral origin of replication is included. Exemplary vectors can be constructed as disclosed by Okayama & Berg (1983). A useful system for stable high level expression of mammalian receptor cDNAs in C127 murine mammary epithelial cells can be constructed substantially as described by Cosman et al. (1986).

The present invention provides a process for producing the recombinant fusion protein of the present invention, comprising culturing a host cell transformed with an expression vector comprising a DNA sequence that encodes said fusion protein under conditions that promote expression of the fusion protein, which is then purified from culture media or cell extracts. Any suitable purification process may be employed, with the procedure of choice varying according to such factors as the type of host cells and whether or not the desired protein is secreted from the host cells. The fusion protein will be secreted into the culture medium when it is initially fused to a signal sequence or leader peptide operative in the host cells, or when the protein comprises soluble forms of the MUC1-EC and carrier polypeptides.

For example, supernatants from expression systems that secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix.

For example, a suitable affinity matrix can comprise antibodies to MUC1-EC or carrier polypeptides. An affinity matrix may be prepared by coupling antibodies to cyanogen bromide-activated Sepharose (Pharmacia) or Hydrazide Affigel (Biorad), according to manufacturer's recommendations. A preferred purification procedure involves sequential immunopurification using antibodies bound to a suitable support. Proteins binding to an antibody specific for MUC1-EC or carrier polypeptide are recovered and contacted with antibody specific for IL-1R on an insoluble support. Proteins immunoreactive with both antibodies may thus be identified and isolated. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. One or more reversed-phase high performance liquid chromatography (RP-HPLC) steps employing hydrophobic RP-HPLC media, e.g., silica gel having pendant methyl or other aliphatic groups, can be employed to further purify a fusion protein composition.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can disrupted by any convenient method, including freeze-thaw cycling, sonication, mechanical disruption, or use of cell, lysing agents.

Fermentation of yeast which express fusion proteins as a secreted protein greatly simplifies purification. Secreted recombinant protein resulting from a large-scale fermentation can be purified by methods analogous to those disclosed by Urdal et al. (1984), involving two sequential, reversed-phase HPLC steps for purification of a recombinant protein on a preparative HPLC column.

Some or all of the foregoing purification steps, in various combinations, can be employed to provide an essentially homogeneous recombinant protein. Recombinant cell culture enables the production of the fusion protein free of those contaminating proteins which may be normally associated with MUC1-EC or carrier polypeptides as they are found in nature, e.g., in cells, cell exudates or body fluids.

As an alternative to production of the inventive chimeric proteins as fusion proteins, the MUC1-EC and carrier polypeptides may be separately produced and purified, and subsequently linked together. Numerous reagents useful for crosslinking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains (e.g., amines on lysine residues and sulfhydryls generated on cysteine residues by reduction), thus linking one polypeptide to another. Examples of such crosslinking reagents are N-maleimidobenzoyl succinimidyl ester and N-hydroxysuccinimide. The reagent and reaction conditions should be chosen such that the cross-linking does not interfere with binding of MUC1-EC to ligands. The MUC1-EC and carrier polypeptides are preferably linked via one of the above-described peptide linkers that functions as a spacer. A peptide linker may be attached to MUC1-EC or carrier polypeptides by any of the conventional procedures used to attach one polypeptide to another. Amino acids having side chains reactive with such reagents may be included in the peptide linker, e.g., at the termini thereof.

III. Antibodies

In regard to the term "antibody" as used for antibodies directed at MUC-1 ligand epitopes, the term is used in the broadest sense and specifically covers monoclonal antibodies (including full length monoclonal antibodies), polyclonal antibodies, multispecific antibodies (e.g., bispecific antibodies), and antibody fragments, so long as they exhibit the desired biological activity.

In regard to dermcidin antibodies, the antibodies are raised against an epitope within SEQ ID NO: 43, and in some embodiments towards an epitope within the amino acid sequence of the mature polypeptide, residues 20 to 110 of SEQ ID NO: 43, and in another embodiment to a recognition site within amino acid residues 20 to 49 of SEQ ID NO: 43. In other embodiments, the dermcidin antibody recognizes an epitope within amino acid residues 20 to 30, or within amino acid residues 25 to 35, or within amino acid residues 30 to 40, or within amino acid residues 45 to 55, of SEQ ID NO: 43.

Methods for generating polyclonal antibodies are well known in the art. Briefly, a polyclonal antibody is prepared by immunizing an animal with an immunogenic composition and collecting antisera from that immunized animal. A wide range of animal species can be used for the production of antisera including rabbit, mouse, rat, hamster, guinea pig and goat. The serum for an immunized animal may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed polypeptide. The immunizing composition is administered in a manner that effectively stimulates antibody producing cells, which may comprise, but is not limited to, administration of MUC1 ligand derived peptides or transgenic cells expressing a MUC1 ligand.

The methods for generating monoclonal antibodies (MAbs) generally begin along the same lines as those for preparing polyclonal antibodies. The use of rats may provide certain advantages (Goding, 1986), but mice are preferred, with the BALB/c mouse being the most routinely used and generally gives a higher percentage of stable fusions. Human antibodies may be prepared from immunized xenomice as described by U.S. Pat. No. 6,075,181 and U.S. Pat. No. 6,150,584, both incorporated herein by reference.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred. Often, a panel of animals will have been immunized and the spleen of animal with the highest antibody titer will be removed for obtaining lymphocytes from the spleen.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas). Selected hybridomas are serially diluted and cloned into individual antibody-producing cell lines, which can then be propagated indefinitely to provide MAbs.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated synthesizer, or by expression of full-length gene or of gene fragments in E. coli or other recombinant microorganisms and cell lines.

The present invention also encompasses various antibody conjugates. Labeled conjugates are useful in various screening and diagnostic uses such as flow cytometry, immunohistochemistry and immuno-quantification methods such as ELISA techniques. Labels used in making versions of the antibodies of the present invention suitable for screening and diagnostic uses include moieties that may be detected directly, such as fluorochromes and radiolabels, as well as moieties, such as enzymes, that must be reacted or derivatized to be detected. Examples of such labels are $^{32}P$, $^{125}I$, $^{3}H$, $^{14}C$, fluorescein and its derivatives, rhodamine and its derivatives, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzandine and the like may be used to tag the antibodies with the above-described fluorescent, chemiluminescent, and enzyme labels. The antibodies may also be labeled with magnetic beads for use in magnetic sorting regimens.

The MAb's of the present invention encompass chimeric MAbs, including, "humanized" forms of non-human (e.g., murine) MAbs. Humanized MAbs are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (FC), typically that of a human immunoglobulin (see Jones et al., 1986; Riechmann et al., 1988; and Presta, 1992). Fully human MAbs are preferred in the therapeutic methods of the present invention.

"Single-chain FV" or "sFv" antibody fragments of the present invention comprise the VH and VL domains of antibody, wherein these domains are present in a single polypeptide chain. Generally, the Fv polypeptide further comprises a polypeptide linker between the VH and VL domains that enables the sFv to form the desired structure for antigen binding (see Pluckthun, 1994).

Aspects of the present invention include methods to inhibit dermcidin-mediated signaling events that lead to inhibition of tumor cell proliferation and induction of tumor cell apoptosis, and sensitization of tumor cells to chemotherapeutic agents, comprising delivering an anti-dermcidin antibody to a cell that expresses MUC1.

IV. Aptamers

Aptamers are specific nucleic acid sequences that bind to a wide array of target molecules with high affinity and specificity. They may be developed by a method commonly known as "in vitro selection" (Ellington et al., 1990), "in vitro evolution" (Joyce, Gene 1989, or "SELEX" (Selective Evolution of Ligands by Evolution; Tuerk et al., 1990). Each SELEX-identified nucleic acid ligand is a specific ligand of a given target compound or molecule. The SELEX process is based on the observation that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand enriched mixture of nucleic acids, then reiterating the steps of binding, partitioning, dissociating and amplifying through as many cycles as desired to yield highly specific high affinity nucleic acid ligands to the target molecule. Thus, this method allows for the screening of large random pools of nucleic acid molecules for a particular functionality, such as binding to small organic molecules (Famulok et al., 1994; Connell et al., 1994; Ellington et al., 1990), and proteins (Jellinek et al., 1993; Tuerk et al., 1992; Tuerk et al., 1993; Schneider et al., 1992). The SELEX process is also described in U.S. Pat. No. 5,475,096 and U.S. Pat. No. 5,270,163, both incorporated herein by reference in their entirety.

The SELEX method also encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 and U.S. Pat. No. 5,580,737 (both herein incorporated by reference) describes highly specific nucleic acid ligands containing one or more nucleotides modified with 2'-amino, 2'-fluoro, and/or 2'-O-methyl. The SELEX method encompasses combining selected oligonucleotides with other selected oligonucleotides and non-oligonucleotide functional units as described in U.S. Pat. No. 5,637,459 and U.S. Pat. No. 5,683,867 (both herein incorporated by reference). These applications allow the combination of the broad array of shapes and other properties, and the efficient amplification and replication properties, of oligonucleotides with the desirable properties of other molecules.

Also encompassed by the present invention are so called Spiegelmers, mirror image aptamers composed of L-ribose or L-2'deoxyribose units. The chiral inversion results in an improved plasma stability compared with natural D-oligonucleotide aptamers. Using in vitro selection, an oligonucleotide that binds to the synthetic enantiomer of a target molecule, e.g. a D-peptide, is isolated. The selected aptamer is then resynthesized in the L-configuration and this Spiegelmer (from the German "speigel" for mirror) will bind to the physiological target with the same affinity and specificity as the aptamer to the mirror-image target. This strategy has been used to identify L-oligonucleotide ligands to a number of targets including gonadotropin-releasing hormone, vasopressin, arginine and adenosine (Leva et al., 2002; Wlotzka et al., 2002; Klussmann et al., 1996; Nolte et al., 1996; Williams et al., 1997, all herein incorporated by reference).

Aptamers of the present invention include those directed towards a recognition site within the amino acid sequence of dermcidin (SEQ ID NO: 43), and in some embodiments towards a recognition site within the amino acid sequence of the mature polypeptide, residues 20 to 110 of SEQ ID NO: 43, and in a preferred embodiment to a recognition site within amino acid residues 20 to 49 of SEQ ID NO: 43. In other embodiments, the aptamer of the present invention is directed towards a recognition site within amino acid residues 20 to 30, or within amino acid residues 25 to 35, or within amino acid residues 30 to 40, or within amino acid residues 45 to 55, of SEQ ID NO: 43.

Aspects of the present invention include methods to inhibit dermcidin expression, inhibition of dermcidin-mediated signaling events that lead to inhibition of tumor cell proliferation and induction of tumor cell apoptosis, and sensitization of tumor cells to chemotherapeutic agents, comprising delivering an aptamer directed towards a recognition site within the dermcidin sequence to a MUC1-expressing cell.

V. Antisense Oligonucleotides and Interfering RNA

The present invention also employs antisense compounds, particularly oligonucleotides, for use in modulating the function of nucleic acid molecules encoding MUC1 ligands, such as dermcidin. Antisense methodology takes advantage of the fact that nucleic acids tend to pair with "complementary sequences." By complementary, it is meant that polynucleotides are those capable of base-pairing according to the standard Watson-Crick complementary rules. The oligonucleotides of the present invention may be targeted wholly or in part to informational sequences, i.e., those coding for a protein, and other associated ribonucleotides such 5'-untranslated regions, 3'-untranslated regions, 5' cap regions and intron/exon junctions. Thus, the invention provides oligonucleotides which specifically hybridize with nucleic acids, preferably mRNA, encoding MUC1 ligands such as dermcidin. The overall effect of interference with mRNA is modulation of expression of dermcidin. Such modulation can be measured in ways that are routine in the art. In addition, effects on cancer cell proliferation, tumor growth and sensitization of cancer cells to other chemotherapeutic agents can be assessed.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment.

The antisense compounds in accordance with this invention preferably comprise from about 4 to about 50 nucleobases. Particularly preferred are antisense oligonucleotides comprising from about 8 to about 30 linked nucleobases. The oligonucleotides used in accordance with this invention may be conveniently and routinely made through the well-known technique of solid phase synthesis.

The terms "specifically hybridizable" and "complementary" are used to indicate a degree of complementarity sufficient to result in stable and specific binding between the antisense oligonucleotide and the target nucleic acid sequence.

An oligonucleotide need not be 100% complementary to its target nucleic acid sequence to be specifically hybridizable. An oligonucleotide considered "specifically hybridizable" when binding of the oligonucleotide to the target interferes with the normal function of the target molecule to cause a loss of utility and decrease in expression of the product protein, and there is a sufficient degree of complementarity to avoid non-specific binding of the oligonucleotide to non-target sequences.

Demcidin is expressed as a 110 amino acid precursor (SEQ ID NO: 43), the mature polypeptide being formed by cleavage of 19 amino acid residue signal peptide. The sequences coding for the first 110 amino acid precursor is provided in SEQ ID NO: 44.

In some embodiments, the antisense oligonucleotide comprises a sequence of at least 4 nucleotides that is complementary to a region os SEQ ID NO: 44. In another embodiment the antisense oligonucleotide is at least 8 nucleotides that is complementary to a region of SEQ ID NO: 44.

The present invention also encompasses expression vectors comprising an expression control system that directs production of a transcript of the foregoing antisense oligonucleotides. In addition, the present invention provides for methods of hybridization comprising providing one of the forgoing antisense oligonucleotides and contacting such oligonucleotide with a nucleic acid comprising the target sequence under conditions that permit hybridization of the oligonucleotide with the nucleic acid. Also included are methods of inhibiting translation of mRNA comprising providing one of the forgoing antisense oligonucleotides and providing a cell comprising mRNA comprising the target sequence and introducing the oligonucleotide into the cell, wherein the oligonucleotide inhibits translation of the mRNA in the cell.

The present invention also encompasses the use of RNA interference ("RNAi") molecules, including small interfering RNA ("siRNA") molecules, as a method of MUC1 gene silencing. siRNA's for mammalian systems are typically composed of double-stranded RNA with 19 to 28, preferable 19 to 23, nucleotide RNA strands, a 2 nucleotide overhand at the 3' end and an optional 5' phosphate group (Yang et al., 2001; Elbashir et al., 2002). Such siRNA's provide a highly active and selective method for reducing the expression of targeted genes by utilizing the RNA interference post-translational gene silencing pathway. Interference of gene expression by interfering RNA is recognized as a naturally occurring mechanism for silencing alleles during development in plants, invertebrates and vertebrates. In this pathway, it is believed that siRNA form a protein complex, sometimes termed an "RNA-induced silencing complexes" ("RISC"), that serve to guide a nucleoside to the mRNA whose sequence matches that of the siRNA, resulting in cleavage of that mRNA (Zamore, 2001). Studies on a variety of gene products of different functions and subcellular localizations have demonstrated the general applicability of the siRNA technique of gene silencing (Harborth et al., 2001).

In some embodiments, double-stranded siRNA complexes are designed using the following guidelines:
(1) a double-stranded RNA complex is composed of a 21-nucleotide sense and 21-nucleotide anti-sense strand, both with a 2-nucleotide 3' overhang, i.e., a 19 nucleotide complementary region;
(2) a 23 nucleotide sequence is chosen in the coding region of the mRNA with a G:C ratio as close to 50% as possible, preferably within about 60% to about 40%, or alternatively within about 70% to about 30% (to create a 21 base pair duplex with overhangs that match the target sequence and have a 19 base pair complementary region, a target sequence of 23 base pairs is needed);
(3) preferably avoid regions within about 75 nucleotides of the AUG start codon or within about 75 nucleotides of the termination codon;
(4) preferably avoid more than three guanosines in a row as poly G sequences can hyperstack and agglomerate;
(5) preferably choose a sequence that starts with AA as this results in siRNA's with dTdT overhangs that are potentially more resistant to nucleases;
(6) preferably the sequence is not homologous to other genes to prevent silencing of unwanted genes with a similar sequence.

A negative control may be included, such a negative control being a nucleotide sequence from a database for a non-existing gene.

Examples of such 21 nucleotide target DNA sequences are provided in SEQ ID NO: 45 through SEQ ID NO: 69.

Also encompassed by the present invention are double-stranded RNA complexes wherein the antisense strand is not exactly complementary to the target mRNA sequence, but can still downregulate MUC-1 ligand expression. Thus, in some embodiments, the antisense strand is a sequence that will hybridize under stringent conditions to the target mRNA sequence. Stringent conditions as used herein means hybridization to filter-bound DNA in 0.5 M NaHPO$_4$, 7% sodium dodecyl sulfate (SDS), 1 mM EDTA at 65° C., and washing in 0.1× sodium chloride/sodium citrate (SSC)/0.1% SDS at 68° C. (Ausubel et al., eds., 1989, Current Protocols in Molecular Biology, Vol. I, John Wiley & Sons, Inc., New York, at p. 2.10.3). In other embodiments, the antisense strand is a sequence that is substantially complementary to the target mRNA sequence. Substantially complementary means that the sequence has up to four mismatched base pairs with the caveat that the double-stranded RNA complex can still effect the downregulation of MUC1 ligands. Downregulation of a MUC1 ligand is determined by inhibition in protein expression by Western blot analysis using specific anti-MUC1 ligand antibodies and/or a RT-PCR analysis specific for MUC1 ligand RNA as compared to a suitable control. In other embodiments, the sense strand has at least a 60% sequence identity to the target mRNA sequence, with the caveat that that the double-stranded RNA complex can still effect the downregulation of the MUC1 ligand. The extent of sequence identity may be greater than 60%, such as at least 65%, at least 70%, at least 75%, at least 80%, at least 85%, or at least 90% sequence identity. "Sequence identity" as used herein, refers to the subunit sequence similarity of two polymeric molecules, herein oligonucleotides. The identity between two sequences is a direct function of the numbering of matching or identical positions. Identity can be measured using the sequence analysis softwear BLASTN. The default parameters for comparing two sequences by BLASTN are reward for match=1, penalty for mismatch=−2, open gap=5, extension gap=2.

The double-standed siRNA complexes of the present invention also encompass hair-pin RNA, in which both strands of a siRNA duplex is included within a single RNA oligonucleotide (Yu et al., 2002; Devroe et al., 2002; Brummelkamp et al., 2002). Thus, for example, the forgoing exemplified complementary sense and antisense RNA sequences may be incorporated into single hairpin RNA oligonucleotides.

In addition to the use of double-stranded siRNA complexes, single strand antisense RNA oligonucleotides can also result in gene silencing utilizing the interference pathway (Martinez et al., 2002). Such single strand antisense RNA is preferably 5' phosphorylated and in mammalian systems is effective from 17 to at least 29 nucleotides in length (Martinez et al., 2002) and in C. elegans from between 22 and 40 nucleotides in length (Tijsterman et al., 2002). Thus, one aspect of the present invention is a 5' phosphorylated RNA olignucleotide of 17 to 40 bases that will hybridize under stringent conditions to SEQ ID NO: 44. Stringent conditions for hydriziation are as defined above. Another aspect of the present invention are 5' phosphorylated RNA oligonucleotides of 17 to 40 bases, wherein the sequences are substantially complementary to a sequence of an equivalent number of bases found in SEQ ID NO: 44, and wherein the oligonucleotide will downregulate the MUC1 ligand of interest. Substantially complementary means that the antisense sequence of the double-stranded siRNA complex has up to four mismatched base pairs as compared with the target mRNA sequence, with the caveat that the 5' phosphorylated RNA oligonucleotide of 17 to 40 bases can still effect the downregulation of the MUC1 ligand. Another aspect of the invention are 5' phosphorylated RNA oligonucleotide of 17 to 40 bases, wherein the sequences have at least a 60% sequence identity to a sequence of an equivalent number of bases in SEQ ID NO: 44, the antisense sequence complementary to the coding region of MUC1 ligand mRNA, and wherein the oligonucleotide will downregulate MUC1 ligand expression.

Aspects of the present invention include methods to inhibit dermicidin expression, inhibition of dermcidin-mediated signaling events that lead to inhibition of tumor cell proliferation and induction of tumor cell apoptosis, and sensitization of tumor cells to chemotherapeutic agents, comprising delivering an antisense RNA of the present invention into a cell that expresses dermcidin.

siRNA oligonucleotides can be synthesized, annealed when required, and purified by methods known in the art (see e.g., Elbashir et al., 2002, herein incorporated by reference). Cells may be transfected with siRNA by use of liposomal and other lipid-mediated transfection methodologies (Hohjoh, 2002; Bertrand et al., 2002; Elbashir et al., 2002, all herein incorporated by reference). Alternatively, siRNA's may be expressed in cells transfected with suitable expression cassettes or vectors (Brummelkamp et al., 2002; Sui et al., 2002; Paul et al., 2002) and by the use of viral mediated delivery mechanisms, e.g., adenoviral and retroviral systems, that may be suitably used to express siRNA in vitro and in vivo (Xia et al., 2002; Devroe & Silver, 2002). In addition to delivery of siRNA molecules, the present invention also encompasses the delivery of longer RNAi molecules by expression constructs.

These longer RNAi molecules may effect gene silencing directly or subsequent to enzymatic cleavage by Dicer. The longer RNAi molecule may be a dsRNA molecule wherein the sense is SEQ ID NO: 42 or a fragment thereof, or in one embodiment is a dsRNA molecule of substantially equivalent size of a dsRNA molecule wherein the sense is SEQ ID NO: 42, wherein substantially similar means±10% relative to the number of bp in the aforementioned dsRNA molecules wherein the sense is SEQ ID NO: 42, wherein the antisense strand will hybridize with SEQ ID 42 under stringent conditions, as defined previously, or in another embodiment are substantially complementary, as defined previously, to SEQ ID 42, or in another embodiment the sense strand has at least 60% sequence identity, as previously defined, to SEQ ID NO 42. In various embodiments, The extent of sequence identity may be greater than 60%, such as at least 65%, at least 70%, at least 75%, at least 80%, at least 85%, or at least 90% sequence identity. In other embodiments, the longer the antisense strand of a dsRNAi molecule may comprise one or more of the sequences SEQ ID NO: 76 though SEQ ID NO: 104, wherein the dsRNAi molecule is about 100 bp, or about 150 bp, or about 200 bp, or about 250 bp, or about 300 bp, or about 350 bp, or about 400 bp in length.

In the context of the present invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

In some embodiments, the oligonucleotides of the present invention may comprise one or more modified internucleoside linkage. Modifications of the normal 3' to 5' phosphodiester linkage include phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Examples of foregoing are taught in WO9905160 and U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697, 5,625,050, 5,652,355, 5,652,356 and 5,750,674, all of which are herein incorporated by reference.

Other non-phosphorus containing modified linkages include those formed by short chain alkyl or cycloalkyl internucleoside linkages, mixed heteroatom and alkyl or cycloalkyl internucleoside linkages, or one or more short chain heteroatomic or heterocyclic internucleoside linkages. Examples include morpholino, siloxane, sulfide, sulfoxide, sulfone, sulfonate, sulfonamide, formacetyl, thioformacetyl, riboacetyl, alkene, sulfamate, methyleneimino, methylenehydrazino, amide backbones; and others having mixed N, O, S, and methylene parts. Examples of foregoing are taught in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, all of which are herein incorporated by reference.

In other embodiments, the oligonucleotides of the present invention may comprise one or more modified sugars, including substituted sugars and sugar mimetics. Examples of 2' substitutents include OH, halo, amino, cyano, or O, S or N linked alkyl, alkenyl or alkynyl groups, wherein the alkyl, alkenyl and alkynyl groups may be substituted or unsubstituted $C_1$-$C_{10}$ alkyl or $C_2$-$C_{10}$ alkenyl and alkynyl, or, alkoxyalkoxy, heterocycloalkyl, heterocycloalkaryl, aminoalkylamino, polyalkylamino, or substituted silyl. Examples include 2'-dimethylaminooxyethoxy, 2'-dimethylaminoethoxyethoxy, 2'-methoxy, 2'-aminopropoxy, 2'-$CH_2$—$CH$=$CH_2$, 2'-O—$CH_2$—$CH$=$CH_2$, and 2'-fluoro. The 2'-modification may be in the arabino position or ribo position. Substitutions at the 2' site of sugars also include Locked Nucleic Acids (LNAs) wherein the 2'-hydroxyl group is linked to the 3' or 4' carbon atom of the sugar ring thereby forming a bicyclic sugar moiety. In one embodiment a —$CH_2$— or —$CH_2CH_2$— group bridges the 2' oxygen atom and the 4' carbon atom. Similar modifications may also be made at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Examples of foregoing are taught in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920, and 6268490 and U.S. Application No. 20020068708A1, all of which are herein incorporated by reference.

In some embodiments, both the sugar and the internucleoside linkages are modified or replaced with novel groups. One such example is referred to as a peptide nucleic acid (PNA) wherein the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Examples of foregoing are taught in U.S. Pat. Nos. 5,539,082; 5,714,331; 5,719,262, and 6,395,474, all of which are herein incorporated by reference.

In further embodiments, the oligonucleotides of the present invention may comprise one or more modified nucleobase. As used in the context of the oligonucleotides of the present invention, "unmodified" nucleobases include the purine bases adenine and guanine, and the pyrimidine bases thymine, cytosine and uracil. Modified nucleobases include other synthetic and natural occurring nucleobases such as 2,6-diamonopurine, 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-fluoroadenine, 2-amino-adenine, 8-azaguanine and 8-azaadenine, 7-deazaguanine and 7-deazaadenine and 3-deazaguanine and 3-deazaadenine. Other examples include tricyclic pyrimidines such as phenoxazine cytidine, phenothiazine cytidine, phenoxazine cytidine, carbazole cytidine, and pyridoindole cytidine. Modified nucleobases may also include those in which the purine or pyrimidine base is replaced with other heterocycles, for example 7-deaza-adenine, 7-deazaguanosine, 2-aminopyridine and 2-pyridone. Examples of foregoing are taught in U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 5,681,941; 5,750,692, 6,005,096; 6,414,112 and Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993, all of which are herein incorporated by reference.

In still further embodiments, the oligonucleotides of the present invention may be linked to one or more moieties or conjugates which enhance the activity, tissue distribution, and/or cellular uptake of the oligonucleotides. Such moieties include but are not limited to, N-9-2-hydroxypropyl)methacrylamide copolymer (Jensen et al., 2002) cholesterol (Letsinger, 1989), cholic acid (Manoharan et al., 1994), a thioether, (Manoharan et al., 1992; Manoharan et al., 1993), a thiocholesterol (Oberhauser et al., 1992), an aliphatic chain, such as dodecandiol or undecyl residues (Saison-Behmoaras et al., 1991; Kabanov et al., 1990; Svinarchuk et al., 1993), a phospholipid, e.g., di-hexadecyl-rac-glycerol or triethyl-ammonium 1,2-di-O-hexadecyl-rac-glycero-3-H-phosphonate (Manoharan et al., 1995; Shea et al., 1990), a polyamine or a polyethylene glycol chain Manoharan et al., 1995), or adamantane acetic acid (Manoharan et al., 1995), a palmityl moiety (Mishra et al., 1995), or an octadecylamine or hexylamino-carbonyl-oxycholesterol moiety (Crooke et al., 1996) or peptides including delivery peptides, e.g., Antennapaedia peptide (Fischer et al., 2002; Zatsepin et al., 2002; Oehlke et al., 2002). Further examples that teach the preparation of such oligonucleotide conjugates include U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, all of which are herein incorporated by reference.

Another aspect of the present invention provides for pharmaceutical compositions comprising an oligonucleotide of the present invention and a pharmaceutically acceptable carrier.

VI. Formulations

For pharmaceutical use, the polypeptides of the present invention are formulated for parenteral, nasal inhalation, particularly intravenous or subcutaneous, delivery according to conventional methods. Intravenous administration will be by bolus injection or infusion over a typical period of one to several hours. In general, pharmaceutical formulations will include an antibody in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington's Pharmaceutical Sciences, Gennaro, ed., Mack Publishing Co., Easton Pa., 1990, which is incorporated herein by reference.

VII. Treatment Methods

Tumors that can be suitably treated with the therapeutic polypeptides or other agents of the present invention include tumors expressing MUC1. Such tumors include, but are not limited to, tumors of the brain (glioblastomas, medulloblastoma, astrocytoma, oligodendroglioma, ependymomas), lung, liver, spleen, kidney, lymph node, small intestine, pancreas, blood cells, colon, stomach, breast, endometrium, prostate, testicle, ovary, skin, head and neck, esophagus, bone marrow, blood and other tissue. The tumor may be distinguished as metastatic and non-metastatic. Pre-malignant lesions may also be suitably treated with the methods of the present invention.

The treatment with MUC1-EC chimeric proteins or other agents of the present invention may precede or follow irradiation and/or chemotherapy by intervals ranging from seconds to weeks and/or be administered concurrently with such treatments. In embodiments where the MUC1-EC chimeric proteins or other agents of the present invention and irradiation and/or chemotherapy are applied separately to the cell, steps should be taken to ensure that a significant period of time does not expire between the time of each delivery, such that the combination of the two or three treatments would still be able to exert an advantageously combined effect on the cell. In such instances, it is contemplated that one would contact the cell with the treatment agents or modalities within amount 0.1 to 25 h of each other and, more preferably, within about 1 to 4 h of each other, with a delay time of only about 1 h to about 2 h being most preferred. In some situations, it is desirable to extend the time period of treatment significantly, however, where several days (2, 3, 4, 5, 6 or 7) or several weeks (1, 2, 3, 4, 5, 6, 7 or 8) lapse between the respective administrations. In any case, the invention contemplates that the MUC1-EC chimeric proteins may be given before, after or even simultaneously with the ionizing radiation and/or chemotherapeutic agent.

Treatment comprises administration of a therapeutically effective dose. In the practice of any of the methods of the invention, or preparation of any of the pharmaceutical compositions, a "therapeutically effective amount" is an amount of antibody which is capable of binding to an antigen associated with the condition to be treated. Accordingly, the effective amount will vary with the subject being treated, as well as the condition to be treated. Determination of dose is within the level of ordinary skill in the art. The antibodies may be administered for acute treatment, over one week or less, often over a period of one to three days or may be used in chronic treatment, over several months or years.

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces cell damage or death when given in conjunction with MUC1-EC chimeric proteins or other agents of the present invention, optionally further combined with a chemotherapeutic agent.

Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Any suitable means for delivering radiation to a tissue may be employed in the present invention, in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

The present invention encompasses the use of MUC1-EC chimeric proteins in combination with chemotherapeutic agents. The chemotherapeutic agents useful in the methods of the invention include the fall spectrum of compositions and compounds that are known to be active in killing and/or inhibiting the growth of cancer cells. The chemotherapeutic agents, grouped by mechanism of action include DNA-interactive agents, antimetabolites, tubulin interactive agents, anti-hormonals, anti-virals, ornithine decarboxylase ("ODC") inhibitors and other cytotoxics such as hydroxyurea. Any of these agents are suitable for use in the methods of the present invention.

DNA-interactive agents include the alkylating agents, e.g., cisplatin, cyclophosphamide; the DNA strand-breakage agents, such as bleomycin; the intercalating topoisomerase II inhibitors, e.g., dactinomycin and doxorubicin; the nonintercalating topoisomerase II inhibitors such as, etoposide and teniposide; and the DNA minor groove binder, plicamycin.

The alkylating agents form covalent chemical adducts with cellular DNA, RNA and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include: nitrogen mustards, such as chlorambucil, cyclophosphamide, ifosfamide, mechlorethamine, melphalan, uracil mustard; aziridine such as thiotepa; methanesulphonate esters such as busulfan; nitroso ureas, such as carmustine, lomustine, streptozocin; platinum complexes such as cisplatin, carboplatin; bioreductive alkylators, such as mitomycin and procarbazine, dacarbazine and altretemine; DNA strand-breaking agents including bleomycin.

Topoisomerases are ubiquitous cellular enzymes which initiate transient DNA strand breaks during replication to allow for free rotation of the strands. The functionality of these enzymes is critical to the replication process of DNA. Without them, the torsional strain in the DNA helix prohibits free rotation, the DNA strands are unable to separate properly, and the cell eventually dies without dividing. Topo I links to the 3'-terminus of a DNA single strand break, while Topo II links to the 5'-terminus of a double strand DNA break. DNA topoisomerase II inhibitors include the following: intercalators such as amsacrine, dactinomycin, daunorubicin, doxorubicin, idarubicin and mitoxantrone; nonintercalators such as etoposide and teniposide; camptothecins including irinotecan (CPT-II) and topotecan. A representative DNA minor groove binder is plicamycin.

The antimetabolites generally exert cytotoxic activity by interfering with the production of nucleic acids by one or the other of two major mechanisms. Some of the drugs inhibit production of the deoxyribonucleoside triphosphates that are the immediate precursors of DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include: folate antagonists such as methotrexate and trimetrexate; pyrimidine antagonists such as fluorouracil, fluorodeoxyuridine, azacitidine, cytarabine, and floxuridine; purine antagonists include mercaptopurine, 6-thioguanine, fludarabine, pentostatin; sugar modified analogs include cytarabine, fludarabine; ribonucleotide reductase inhibitors include hydroxyurea.

Tubulin interactive agents interfere with cell division by binding to specific sites on Tubulin, a protein that polymerizes to form cellular microtubules. Microtubules are critical cell structure units. When the interactive agents bind on the protein; the cell cannot properly form microtubules. Tubulin interactive agents include vincristine and vinblastine, both alkaloids and the taxanes (paclitaxel and docetaxel).

Although their mechanisms of action are different, both taxanes and vinca alkaloids exert their biological effects on the cell microtubles. Taxanes act to promote the polymerization of tubulin, a protein subunit of spindle microtubules. The end result is the inhibition of depolymerization of the microtubles, which causes the formation of stable and nonfunctional microtubules. This disrupts the dynamic equilibrium within the microtubule system, and arrests the cell cycle in the late $G_2$ and M phases, which inhibits cell replication.

Like taxanes, vinca alkaloids also act to affect the microtuble system within the cells. In contrast to taxanes, vinca alkaloids bind to tubulin and inhibit or prevent the polymerization of tubulin subunits into microtubules. Vinca alkaloids also induce the depolymerization of microtubules, which inhibits microtubule assembly and mediates cellular metaphase arrest. Vinca alkaloids also exert effects on nucleic acid and protein synthesis; amino acid, cyclic AMP, and glutathione synthesis; cellular respiration; and exert immunosuppressive activity at higher concentrations.

Antihormonal agents exert cytotoxic activity by blocking hormone action at the end-receptor organ. Several different types of neoplasm require hormonal stimulation to propagate cell reproduction. The antihormonal agents, by blocking hormone action, deprive the neoplastic cells of a necessary stimulus to reproduce. As the cells reach the end of their life cycle, they die normally, without dividing and producing additional malignant cells. Antihormonal agents are typically derived from natural sources and include: estrogens, conjugated estrogens and ethinyl estradiol and diethylstibesterol, chlortrianisen and idenestrol; progestins such as hydroxyprogesterone caproate, medroxyprogesterone, and megestrol; androgens such as testosterone, testosterone propionate; fluoxymesterone, methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include prednisone, dexamethasone, methylprednisolone, and prednisolone.

Leutinizing-releasing hormone agents or gonadotropin-releasing hormone antagonists are used primarily in the treatment of prostate cancer. These include leuprolide acetate and goserelin acetate. They prevent the biosynthesis of steroids in the testes.

Anti-hormonal agents include antiestrogenic agents such as tamoxifen, antiandrogen agents such as flutamide, and antiadrenal agents such as mitotane and aminoglutethimide.

ODC inhibitors inhibit cancerous and pre-cancerous cell proliferation by depleting or otherwise interfering with the activity of ODC, the rate limiting enzyme of polyamine biosynthesis important to neoplastic cell growth. In particular, polyamine biosynthesis wherein ornithine is converted to the polyamine, putrescine, with putrescine being subsequently converted to spermidine and spermine appears to be an essential biochemical event in the proliferation of neoplastic growth in a variety of cancers and cancer cell lines and the inhibition of ODC activity or depletion of ODC in such neoplastic cells has been shown to reduce polyamine levels in such cells leading to cell growth arrest; more differentiated cell morphology and even cellular senescence and death. In this regard, ODC or polyamine synthesis inhibitors are considered to be more cytotoxic agents functioning to prevent cancer reoccurrence or the conversion of pre-cancerous cells to cancerous cells than cytotoxic or cell killing agents. A suitable ODC inhibitor is eflornithine or α-difluoromethyl-ornithine, an orally available, irreversible ODC inhibitor, as well as a variety of polyamine analogs which are in various stages of pre-clinical and clinical research.

Other cytotoxics include agents which interfere or block various cellular processes essential for maintenance of cellular functions or cell mitosis as well as agents which promote apoptosis. In this regard, hydroxyurea appears to act via inhibitors of the enzyme ribonucleotide reductase whereas asparaginase enzymatically converts asparagine into non-functional aspartic acid thereby blocking protein synthesis in a tumor.

Compositions of MUC1-variant specific therapeutic antibodies of the present invention can also be used in combination with antibodies to HER-2, such as Trastuzumab (Herceptin (H), or antibodies to the epidermal growth factor receptor ("EGFR"), such as ERBITUX™ (IMC-C225). In addition, the present invention also encompasses the use of MUC1 domain antagonists in combination with epidermal growth factor receptor-interactive agents such as tyrosine kinase inhibitors. Tyrosine kinase inhibitors suitably include imatinib (Novartis), OSI-774 (OSI Pharmaceuticals), ZD-1839 (AstraZeneca), SU-101 (Sugen) and CP-701 (Cephalon).

When used in the treatment methods of the present invention, it is contemplated that the chemotherapeutic agent of choice can be conveniently used in any formulation that is currently commercially available, and at dosages which fall below or within the approved label usage for single agent use.

VIII. Screening Methods

The present invention also provides for methods of screening for compounds that can inhibit the binding of dermcidin to MUC1. Thus, the method of the present invention-provides a MUC1 polypeptide comprising the MUC1 ECD sequence. Such a MUC1 polypeptide includes full-length MUC1 and splice variants such as MUC1Y, MUC1X or MUC1Z. The MUC1 may be provided be means of expression on a cell, which may be a cell transfected with a vector that expresses the MUC1 polypeptide (see e.g., Ren et al., 2002; Li et al., 2003), or it may be a recombinant peptide, with also may be a GST-fusion peptide (see e.g., Ren et al., 2002), or as a FC fusion protein (see Example 1). The method also provides for a dermcidin polypeptide, which may be the precursor polypeptide, the mature polypeptide, or a polypeptide equivalent to the Y-P30 polypeptide.

In some embodiments, either an isolated MUC1 polypeptide or an isolated dermcidin polypeptide may be immobilized. The free polypeptide species may be tagged with a suitable indicator such as a fluorescent label (e.g., FITC), biotin, enzyme indicator, or other suitable indicators generally known by those of skill in the art. Screening of inhibition of binding of the two polypeptide species may be undertaken by introducing candidate compounds.

In some embodiments, an isolated dermcidin is provided to a MUC1 polypeptide expressed in a cell. Candidate compounds can be screened by the observation of an inhibition of a demcidin-induced response, e.g., proliferation, anchorage independent growth, internalization of MUC1 or translocation of the MUC1 cytoplasmic domain to subcellular organelles such as the nucleus or mitochondria.

EXAMPLES OF THE INVENTION

Example 1

Preparation of MUC1Y-EC-FC Fusion Protein

A chimeric protein containing the human FC region and the extracellular domain of MUC1-Y was prepared for use as an antigen. Full-length cDNA of MUC1-Y (Baruch et al., 1997) was constructed in three steps of PCR. In the first PCR, cDNA coding for MUC1 signal peptide was made with the MUC1 primers:

```
5'-CTAGCTAGVATGACACCGGGCACCCAGTC-3',
and

5'-GGAATTAAAAGCATTCTTCTCAGTAG-3'.
```

Then the primers:

```
5'-AATGCTTTTAATTCCTCTCTG-3',
and

5'-CTTAAGCTACAAGTTGGCAGAAGT-3',
``` were used for the second PCR to produce cDNA of MUC1-Y without signal peptide. The mixture of first and second PCR products was taken as a template, and the full-length of MUC1-Y cDNA was amplified in the third PCR with the primers:

```
5'CTAGCTAGC-ATGACACCGGGCACCCAGTC-3',
and

5'-CTTAAGCTACAAGTTGGCAGAAGT-3'.
```

After digestion of both MUC1-Y cDNA and pIRESpuro2 vector (Clontech Lab., Inc) with Nhe I and Aft II, DNA fragments were separated on 1.2% agarose gel. MUC1-Y DNA was purified and ligated into pIRESpuro2 vector. The construct was confirmed by both enzymes digestion and DNA sequencing.

The cDNA sequence of a human IgG1 FC fragment (SEQ ID NO: 36) with a KL liner sequence at the amino-terminus was cloned in to the expression vector, pEF6/V5.His Invitrogen Cat #V96120), resulting in pEF6/V5.His-hFc. The cDNA of the extracellular domain of MUC1-Y (MUC1-Yex) was amplified by PCR using the primers:

MUC1/Yex-N-NheI:
5'-CCC ACC GCT AGC ACC ACC ACC ATG ACA CCG-3',
and

MUC1/Yex-C-HindIII:
5'-CCA GCC AAG CTT CCC AGC CCC AGA CTG GGC-3', and cloned, in frame, upstream of the human FC sequence in pEF6/V5.His-hFc resulting in pEF6/V5.His-MUC1/Yex-hFc. The expression plasmid was confirmed by DNA sequencing.

For stable transfection, the expression plasmid was transfected into CHO K1 cells by lipofectamine. Transfected CHO K1 cells were selected by antibiotics, and single clones were selected and expanded. Secreted chimeric protein was purified by chromatography using protein A column chromatography, depletion of bovine IgG and buffer exchange and concentration.

The chimeric protein as expressed contained the MUC1-Y extracellular domain plus the N-terminal sequence (SEQ ID NO: 1):

MTPGTQSPFFLLLLLTVLTATTAPKPATVVTGSGHASSTPGGEKETSATQ

RSSVPSSTEKNAFNSSLEDPSTDYYQELQRDISEMFLQIYKQGGFLGLSN

IKFRPGSVVVQLTLAFREGTINVHDVETQFNQYKTEAASRYNLTISDVSV

SDVPFPFSAQSGAG

Upon secretion from the cell, the N-terminal sequence was cleaved resulting in a human FC chimeric protein containing the 102 amino acid MUC1-Y extracellular sequence (SEQ ID NO: 11): FNSSLEDPSTDYYQELQRDISEMFL-QIYKQGGFLGLSNIKFRPGSVVVQL TLAFREGTIN-VHDVETQFNQYKTEAASRYNLTISDVS-VSDVPFPFSAQSGAG The polypeptide and polynucleotide sequences of the fusion protein are as shown by SEQ ID NO: 70 and SEQ ID NO: 71 respectively.

PAGE gel analysis under unreduced and reduced conditions indicated that the fusion protein forms a dimmer.

Example 2

Identification of MUC1 Ligands Utilizing MUC1Y-EC-FC Fusion Protein

An affinity column was prepared by immobilizing 1 mg fusion protein on 1 ml of packed Aminolink agarose (Pierce) per manufacturer's instructions. Conditioned medium, from ZR-75-1 cells, neat or diluted with 3 vols of cold 20 mM Tris-HCl, pH 7.4 was salt extract (0.75 M NaCl, 2 mM Na2EDTA, Boehringer protease inhibitors, 10 mM MES, pH 6.2) and passed through the affinity column in a cold room at a rate of 1 ml/min. The column was washed with Dulbecco's phosphate-buffered saline and eluted with 2 M NaCl, 2 mM $Na_2EDTA$. Eluted fractions were monitored in a spectrophotometer at a wavelength of 280 nm.

Eluate was concentrated and desalted using Biomax-5K filtration unit (Millipore) to 50-100 μl. Samples for electrophoresis were prepared by mixing of concentrated eluate with Tricine sample buffer (Bio-Rad), run in 16.5% Tris-Tricine Ready gel (Bio-Rad), and stained with Coomassie Simply Blue (Invitrogen). Stained gel bands were excised, destained in 50% ethanol, 10% acetic acid, soaked in water and then— in 50 mM ammonium bicarbonate. Standard procedures utilizing DTT and iodoacetic acid were used for reduction and alkylation of proteins. Following washing in water, excised pieces of gel were cut into smaller pieces, dehydrated in acetonitrile, dried, and rehydrated in 50 mM ammonium bicarbonate containing trypsin (Promega). After incubation for several hours at 30° C., generated peptides were extracted and run on RP HPLC (C18, Wako) column. Collected peaks were analyzed in ion trap MS instrument.

Dermcidin and PLU-1 were identified as putative ligands.

Example 3

In Vitro Treatment Models

Cells that endogenously express MUC-1 such as A549 human non-small cell lung cancer; T-47D and ZR-75-1 human breast cancer cells. Non-MUC1-expressing cells can be transfected, e.g., HCT116 or SW80 human colon cancer cells can be transfected with pIRES-puro2 or pIRESpuro2-MUC1 as described (Li et al., 2001b).

HCT116 and SW80 cells are cultured in Dulbecco's modified Eagle's medium/F12 with 10% heat-inactivated fetal calf serum (FCS), 100 units/ml penicillin, 100 μg/ml streptomycin and 2 mM L-glutamate. A549, T-47D and ZR-75-1 cells are grown in RPMI1640 medium supplemented with 10% fetal bovine serum (FBS), 100 units/ml of penicillin and 100 μg/ml of streptomycin.

Cells are treated with a MUC1-EC fusion protein, e.g., the MUC1Y-EC-FC fusion protein of Example 1, alone or in addition to chemotherapeutic agents such as cis-platin (CDDP) or etopside or agents that induce oxidative stress such as $H_2O_2$. For example, cells may be treated with 10, 50 or 100 μM CDDP for 8, 24, or 48 hrs in the absence or presence of an effective amount of a MUC1-EC fusion protein.

Cell are evaluated apoptosis by analysis of sub-G1 DNA, TUNEL staining or annex-V staining (Ren et al., 2004).

Example 4

In Vivo Treatment Model

MUC1 transfected mice, e.g., HCT116/vector or HCT116/MUC1 cells ($1\times10^6$), or endogenously expressing MUC1 cells, e.g., ZR-75-1 cells ($1\times10^7$) are injected subcutaneously in the flanks of 4 to 6-week old female nude (nu/nu) mice. Tumors (e.g., 4 mice/group) are measured twice a week in control and mice treated with suitable amounts of a MUC1-EC fusion protein. Tumor volumes are calculated by the following formula: ½(length×width$^2$). Experiments are terminated when tumor volume exceeded 2 cm$^3$.

REFERENCES

The following references, to the extent that they provide exemplary procedural or other details supplementary to those set forth herein, are specifically incorporated herein by reference.

Barret et al., Int. J. Cancer, 101:581-588, 2002.
Baruch et al., Int. J. Cancer 71:741-749, 1997.
Beier et al., Nature 300:724, 1982.
Bertrand et al., Biochem. Biophys. Res. Commun., 296:1000-10004, 2002.
Bitter et al., Proc. Natl. Acad. Sci. USA 81:5330, 1984.
Bolivar et al., Gene 2:95, 1977.
Brummelkamp et al., Science, 296:550-553, 2002.
Chang et al., Nature 275:615, 1978.
Cosman et al., Mol. Immunol. 23:935, 1986.

Connell et al., Biochemistry, 32:5497-5502, 1994.
Crooke et al., J. Pharmacol. Exp. Ther., 277:923-937, 1996.
Cunningham et al., J. Neurosci., 18:7047-7060, 1998.
Cunningham et al., Exp. Neurol., 163:457-468, 2000.
Cunningham et al., Exp. Neurol., 177:32-39, 2002.
Devroe & Silver, BMC Biotechnol, 2:15, 2002.
Elbashir et al., Methods, 26:199-213, 2002.
Ellington et al., Nature, 346:818-822, 1990.
Famulok et al., Am. J. Chem. Soc., 116:1698-1706, 1994.
Fiers et al., Nature 273:113, 1978.
Fisher et al., J. Biol. Chem., 277:22980-22984, 2002.
Gendler et al., J Biol Chem 263, 12820-12823, 1988.
Gluzman, Cell 23:175, 1981.
Goeddel et al., Nature 281:544, 1979.
Goeddel et al., Nucl. Acids Res. 8:4057, 1980.
Harborth et al., J. Cell Sci., 114:4557-4565, 2001.
Hess et al., J. Adv. Enzyme Reg. 7:149, 1968.
Hinnen et al., Proc. Natl. Acad. Sci. USA 75:1929, 1978.
Hitzeman et al., J. Biol. Chem. 255:2073, 1980.
Hohjoh, FEBS Lett., 521:195-199, 2002.
Holland et al., Biochem. 17:4900, 1978.
Jellinek et al., Proc. Natl. Acad. Sci., USA 90:11227-11231, 1993.
Jensen et al., Bioconjug. Chem., 13:975-984, 2002.
Jones et al., Nature 321:522-525, 1986.
Joyce, Gene, 82:83-87, 1989.
Julian & Carson, Biochem. Biophys. Res. Commun., 293: 1183-1190, 2002.
Kabanov et al., FEBS Lett., 259:327-330, 1990.
Klussmann et al., Nat. Biotechnol., 14:1112-1115, 1996.
Kufe et al., Hybridoma 3, 223-232, 1984.
Kurjan et al., Cell 30:922, 1982.
Letsinger et al., Proc. Natl. Acad. Sci. USA, 86:6553-6556, 1989.
Leva et al., Chem. Biol., 9:351-359, 2002.
Li et al., Mol Cell Biol 18, 7216-7224, 1998.
Li et al., J Biol Chem 276, 6061-6064 2001a.
Li et al. J Biol Chem 276, 35239-35242, 2001b.
Li et al., Cancer Biol Ther 2, 187-193 2003a.
Li et al., Oncogene, 22:6107-6110, 2003b.
Li et al., Mol Cancer Res, 1:765-775, 2003c.
Ligtenberg et al., Cancer Res 52, 223-232, 1992.
Luckow & Summers, Bio/Technology 6:47, 1988.
Maniatis, Molecular Cloning: A Laboratory Manual, Cold Spring Harbor Laboratory, p. 412, 1982.
Manoharan et al., Ann. N.Y. Acad. Sci., 660:306-309, 1992
Manoharan et al., Bioorg. Med. Chem. Let., 3:2765-2770, 1993
Manoharan et al., Bioorg. Med. Chem. Let., 4:1053-1060, 1994.
Manoharan et al., Tetrahedron Lett., 36:3651-3654; 1995.
Manoharan et al., Nucleosides & Nucleotides, 14:969-973, 1995.
Martinez et al., Cell, 110:563-574, 2002.
Mishra et al., Biochim. Biophys. Acta, 1264:229-237, 1995.
Nolte et al., Nat. Biotechnol., 14:1116-1119, 1996.
Oberhauser et al., Nucl. Acids Res., 20:533-538, 1992.
Obermair et al., Int. J. Cancer., 100:166-171, 2002.
Okayama & Berg, Mol. Cell. Biol. 3:280, 1983.
Oehlke et al., Eur. J. Biochem., 269:4025-4032, 2002.
Oosterkamp et al., Int. J. Cancer, 72:87-94, 1997.
Parry et al., Biochem. Biophys. Res. Commun., 283:715-720, 2001.
Paul et al., Nature Biotechnol., 20:505-508, 2002.
Pluckthun in The Pharmacology of Monoclonal Antibodies, vol. 113:269-315, 1994.
Porter et al., Proc. Natl. Acad. Sci. USA, 100:10931-10936, 2003.
Pouwels et al., Cloning Vectors: A Laboratory Manual, Elsevier, N.Y., 1985.
Presta, Curr. Op. Struct Biol. 2:593-596, 1992.
Ren et al., J Biol Chem 277, 17616-17622, 2002.
Ren et al., Cancer Cell, 5, 163-175, 2004.
Riechmann et al., Nature 332:323-329, 1988.
Russell et al. J. Biol. Chem. 258:2674, 1982.
Saison-Behmoaras et al., EMBO J., 10:11111-1118, 1991.
Schneider et al., J. Mol. Biol., 228:862-869, 1992.
Schroeder et al. J Biol Chem 276, 13057-13064, 2001.
Shea et al., Nucl. Acids Res., 18:3777-3783, 1990.
Siddiqui et al, Proc Natl Acad Sci USA 85, 2320-2323, 1988.
Smith & Waterman, Adv. Appl. Math., 2:482-489, 1981.
Sui et al., Pro. Nat'l. Acad. Sci. U.S.A., 99:5515-5520, 2002.
Svinarchuk et al., Biochimie, 75:49-54, 1993.
Tijsterman et al., 295:694-697, 2002.
Tuerk et al., Science, 249:505-510, 1990.
Tuerk et al., Proc. Natl. Acad. Sci., USA 89:6988-6992, 1992.
Tuerk et al., Gene, 137:33-39, 1993.
Urdal et al., J. Chromatog. 296:171, 1984.
Williams et al., Proc. Nat'l. Acad. Sci. USA, 94:11285-11290, 1997.
Woltzka et al., Proc. Nat'l. Acad. Sci. USA, 99:8898-8902, 2002.
Xia et al., Nature Biotechnol., 20:1006-1010, 2002.
Yamamoto et al., J Biol Chem 272, 12492-12494, 1997.
Yang et al., Mol. Cell. Biol., 21:7807-7816, 2001.
Yeh et al., Proc. Natl. Acad. Sci. USA, 89:1904-1908, 1992.
Yu et al., Proc. Nat'l. Acad. Sci. U.S.A, 99:6047-6052, 2002.
Zamore, Nature Struct. Biol., 8:746-750, 2001.
Zatsepin et al., Bioconjug. Chem. 13:822-830, 2002.
Zrihan-Licht et al., Eur. J. Biochem., 224:787-795, 1994.

---

The invention claimed is:

1. A MUC1 chimeric protein comprising a first polypeptide sequence and a second polypeptide sequence, wherein said first polypeptide sequence is a MUC1-EC polypeptide wherein amino-terminal tandem repeat sequences of MUC1-EC are deleted and said second polypeptide sequence is a human immunoglobulin FC polypeptide or a human albumin polypeptide.

2. The MUC1 chimeric protein of claim 1, wherein said MUC1-EC polypeptide is selected from the group consisting of SEQ ID NO: 15, SEQ ID NO: 17, SEQ ID NO: 19, and SEQ ID NO: 23.

3. The MUC1 chimeric protein of claim 1, wherein said human immunoglobulin FC polypeptide is a human IgG FC polypeptide.

4. The MUC1 chimeric protein of claim 3, wherein said IgG FC polypeptide is a IgG1 or IgG2 FC polypeptide.

5. The MUC1 chimeric protein of claim 3, further comprising a second MUC1 chimeric protein comprising a human immunoglobulin FC polypeptide, wherein said MUC1 chimeric protein and said second MUC1 chimeric protein form a dimer by means of disulfide bridge formation between the hinge region of the human immunoglobulin FC polypeptide of said MUC1 chimeric protein and the hinge region of the human immunoglobulin FC polypeptide of said second MUC1 chimeric protein.

6. The MUC1 chimeric protein dimer of claim 5, wherein said MUC1 chimeric protein dimer comprises two different MUC1-EC polypeptides.

7. The MUC1 chimeric protein of claim 1, wherein said MUC1 chimeric protein is a fusion protein.

8. The MUC1 chimeric protein of claim 1, wherein said MUC1-EC polypeptide is SEQ ID NO:19.

9. A pharmaceutical composition comprising the MUC1 chimeric protein of claim 1 and a pharmaceutically acceptable carrier.

10. A method of inhibiting the proliferation of a MUC1-expressing cancer cell comprising contacting said MUC1-expressing cancer cell with an effective amount of a MUC1 chimeric protein comprising a first polypeptide sequence and a second polypeptide sequence, wherein said first polypeptide sequence is a MUC1-EC polypeptide and said second polypeptide sequence is a human immunoglobulin FC polypeptide or a human albumin polypeptide.

11. A method of killing a MUC1-expressing cancer cell comprising contacting said MUC1-expressing cancer cell with an effective amount of a MUC1 chimeric protein comprising a first polypeptide sequence and a second polypeptide sequence, wherein said first polypeptide sequence is a MUC1-EC polypeptide and said second polypeptide sequence is a human immunoglobulin FC polypeptide or a human albumin polypeptide.

12. The method of claim 11, further comprising contacting said MUC1-expressing cancer cell with an effective amount of a chemotherapeutic agent.

13. The method of claim 11, further comprising exposing said MUC1-expressing cancer cell with an effective amount of ionizing radiation.

14. A method of treating a MUC1-expressing cancer in a patient comprising administering an effective amount of MUC1 chimeric protein comprising a first polypeptide sequence and a second polypeptide sequence, wherein said first polypeptide sequence is a MUC1-EC polypeptide and said second polypeptide sequence is a human immunoglobulin FC polypeptide or a human albumin polypeptide.

* * * * *